(12) United States Patent
Slepicka et al.

(10) Patent No.: US 8,287,724 B2
(45) Date of Patent: Oct. 16, 2012

(54) DIALYSIS FLUID MEASUREMENT SYSTEMS USING CONDUCTIVE CONTACTS

(75) Inventors: James S. Slepicka, Genoa City, WI (US); Mark Perry, McHenry, IL (US); William Chan, Lake in the Hills, IL (US); Richard Kienman, Tampa, FL (US); Angel M. Lasso, Tampa, FL (US); Donald Busby, Tampa, FL (US); Rodolfo G. Roger, Clearwater, FL (US); Michael E. Hogard, Odessa, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1502 days.

(21) Appl. No.: 11/773,644

(22) Filed: Jul. 5, 2007

(65) Prior Publication Data
US 2009/0012452 A1    Jan. 8, 2009

(51) Int. Cl.
*B01D 61/30* (2006.01)
*B01D 61/32* (2006.01)

(52) U.S. Cl. ...... 210/85; 210/96.2; 210/149; 210/321.6; 210/321.71; 210/258; 210/646; 604/5.01; 604/6.09; 604/29; 604/65

(58) Field of Classification Search ............. 210/85, 210/96.2, 149, 321.6, 321.71, 645–647, 258; 604/5.01, 6.01, 6.09, 29, 65–67
See application file for complete search history.

(56) References Cited

U.S. PATENT DOCUMENTS

| | | | |
|---|---|---|---|
| 3,601,255 A | | 8/1971 | Pecker et al. |
| 3,686,926 A | | 8/1972 | Miller |
| 3,882,020 A | * | 5/1975 | Cere ........................... 210/85 |
| 3,953,790 A | | 4/1976 | Ebling et al. |
| 3,979,665 A | | 9/1976 | Ebling et al. |
| 4,035,719 A | * | 7/1977 | Anderson ................. 324/443 |
| 4,064,035 A | | 12/1977 | Fukasawa |
| 4,079,007 A | * | 3/1978 | Hutchisson ................. 210/85 |
| 4,160,946 A | | 7/1979 | Frigato |
| 4,298,938 A | | 11/1981 | Wang et al. |
| 4,309,660 A | | 1/1982 | Stephen |
| 4,362,994 A | | 12/1982 | Goldsmith et al. |
| 4,365,200 A | | 12/1982 | Goldsmith |
| 4,399,036 A | * | 8/1983 | Babb et al. ................. 210/638 |

(Continued)

FOREIGN PATENT DOCUMENTS
EP    0165751    12/1985
(Continued)

OTHER PUBLICATIONS

Written Opinion of the International Searching Authority for International Application No. PCT/US2008/064857 mailed on Jan. 19, 2009.

*Primary Examiner* — Joseph Drodge
(74) *Attorney, Agent, or Firm* — K&L Gates LLP

(57) ABSTRACT

A dialysis system instrument includes a dialysis instrument, a disposable pumping and valving cassette apparatus operable with pumping and valving actuators of the dialysis instrument, the disposable cassette including an electronic cell and electronics associated with the electronic cell, the electronics configured to determine an electrical property of a solution flowing through the electronic cell of the disposable apparatus.

21 Claims, 15 Drawing Sheets

U.S. PATENT DOCUMENTS

| | | |
|---|---|---|
| 4,403,984 A | 9/1983 | Ash et al. |
| 4,496,906 A | 1/1985 | Clack |
| 4,644,285 A | 2/1987 | Britton |
| 4,682,105 A | 7/1987 | Thorn |
| 4,751,466 A | 6/1988 | Colvin et al. |
| 4,812,239 A | 3/1989 | Mills et al. |
| 5,059,902 A | 10/1991 | Linder |
| 5,077,525 A | 12/1991 | West |
| 5,089,776 A | 2/1992 | Furukawa |
| 5,130,639 A | 7/1992 | Hachey |
| 5,157,332 A | 10/1992 | Reese |
| 5,225,783 A | 7/1993 | Suzuki |
| 5,247,434 A | 9/1993 | Peterson et al. |
| 5,334,932 A | 8/1994 | Nielsen |
| 5,414,368 A | 5/1995 | Ogawa |
| 5,480,511 A | 1/1996 | Barbee et al. |
| 5,485,083 A | 1/1996 | Pulice |
| 5,486,286 A | 1/1996 | Peterson et al. |
| 5,487,827 A | 1/1996 | Peterson et al. |
| 5,491,097 A | 2/1996 | Ribi et al. |
| 5,504,430 A | 4/1996 | Andersson |
| 5,611,904 A | 3/1997 | Cole et al. |
| 5,716,531 A | 2/1998 | Kenley et al. |
| 5,744,027 A | 4/1998 | Connell et al. |
| 6,284,131 B1 | 9/2001 | Hogard et al. |
| 6,614,212 B2 | 9/2003 | Brugger et al. |
| 6,653,841 B1 | 11/2003 | Koerdt et al. |
| 6,995,563 B2 | 2/2006 | Talutis |
| 7,022,098 B2 | 4/2006 | Wariar et al. |
| 7,052,480 B2 | 5/2006 | Han et al. |
| 7,138,088 B2 | 11/2006 | Wariar et al. |
| 7,279,903 B2 | 10/2007 | Quackenbush et al. |
| 7,303,680 B2 | 12/2007 | Connell et al. |
| 7,318,892 B2 | 1/2008 | Connell et al. |
| 7,772,854 B2 * | 8/2010 | Rezvani .................. 324/691 |
| 2003/0195454 A1 | 10/2003 | Wariar et al. |
| 2004/0254513 A1 * | 12/2004 | Shang et al. ............. 604/5.01 |
| 2005/0242034 A1 | 11/2005 | Connell et al. |
| 2007/0126794 A1 | 6/2007 | Schick et al. |
| 2007/0253463 A1 | 11/2007 | Perry et al. |
| 2008/0208111 A1 * | 8/2008 | Kamen et al. ............... 604/29 |
| 2008/0240929 A1 * | 10/2008 | Kamen et al. ............... 417/32 |
| 2008/0253427 A1 | 10/2008 | Kamen et al. |

FOREIGN PATENT DOCUMENTS

| | | |
|---|---|---|
| EP | 0165751 A2 | 12/1985 |
| WO | 97/09074 A2 | 3/1997 |
| WO | 9709074 | 3/1997 |
| WO | 2005/089832 A2 | 9/2005 |
| WO | 2005089832 | 9/2005 |
| WO | PCT/US2008/064857 | 10/2008 |

* cited by examiner

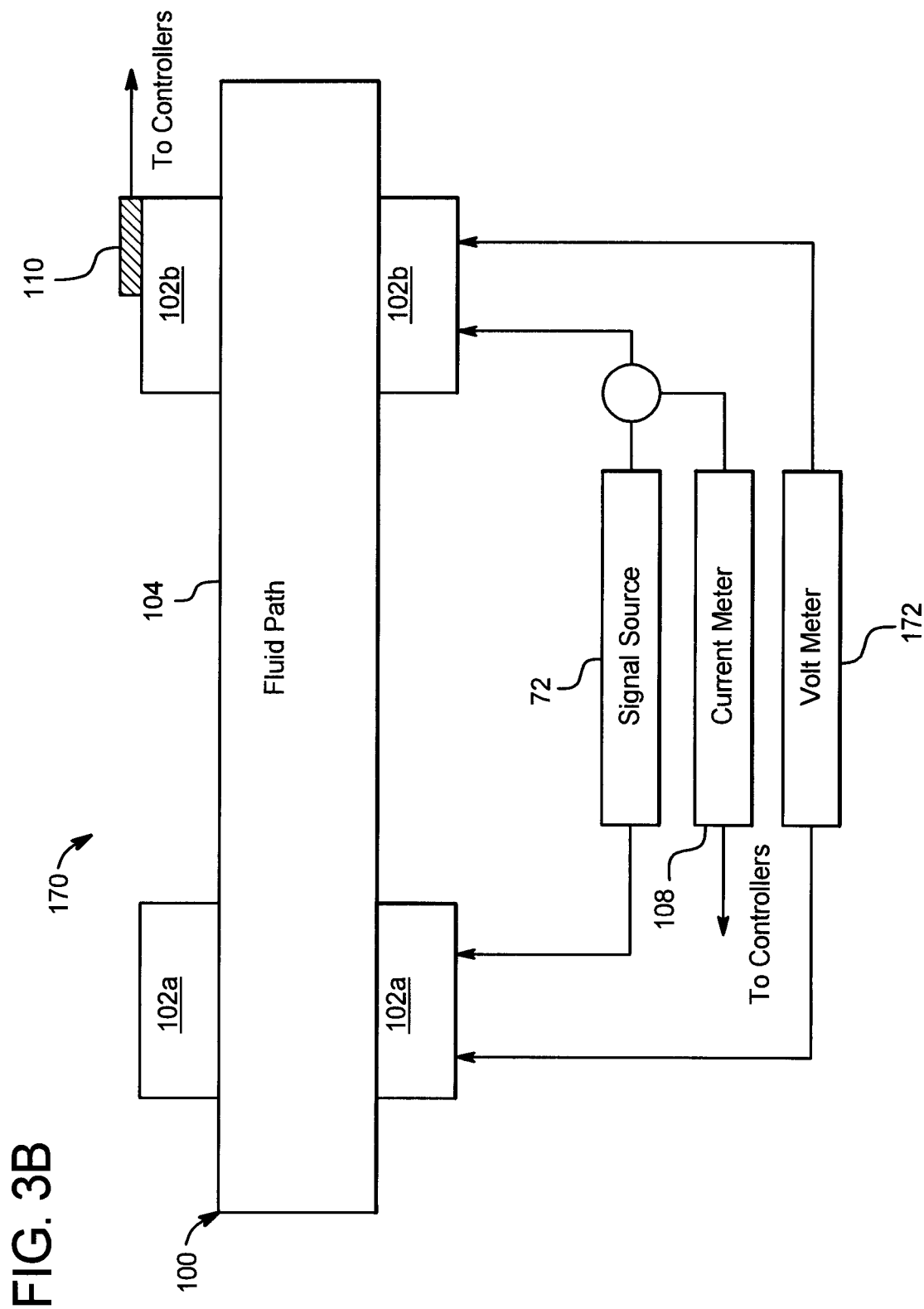

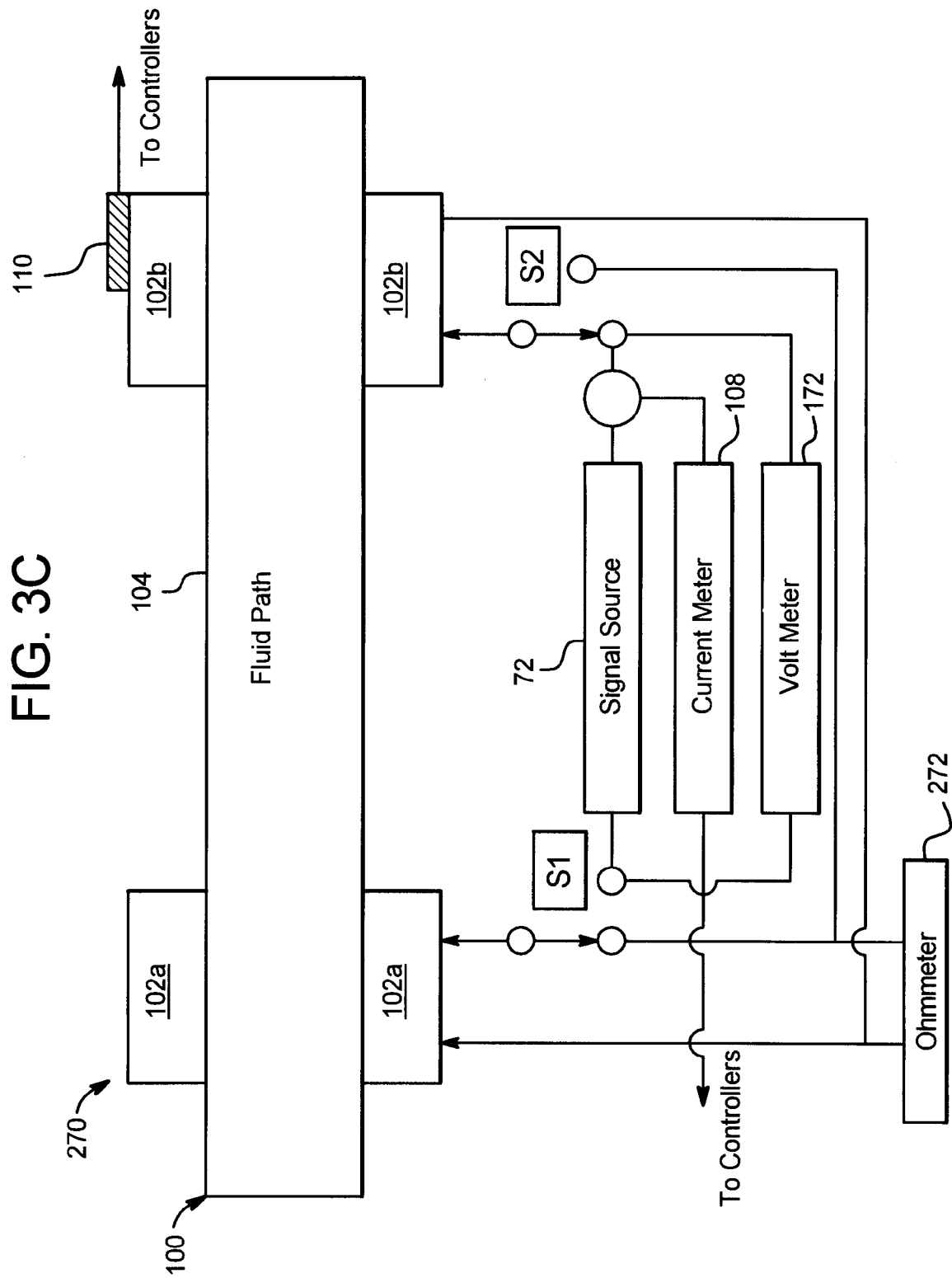

DIALYSIS FLUID MEASUREMENT SYSTEMS USING CONDUCTIVE CONTACTS

BACKGROUND

The present disclosure relates to healthcare/medication delivery systems. In particular, the present disclosure relates to testing and controlling the quality of medical fluids being delivered to a patient in healthcare/medication delivery systems.

Complex medical fluids are often administered to a patient through a variety of different medication delivery systems. For example, a medication delivery system such as a dialysis machine for performing peritoneal dialysis on a patient having decreased or total loss of kidney function uses a dialysis solution or dialysate that removes waste from the patient's bloodstream. In another example, infusion pumps for medication delivery deliver liquid drugs or medical fluids, such as morphine or the like to a patient based upon parameters entered into the medication delivery system. The above fluids can be a homogenous liquid, a mixed solution or a solution that includes particulates in a buffer liquid. Infusion pumps can for example be rotary, linear or roller type peristaltic pumps or piezoelectric pumps.

The concentration or presence of the medication in the solution being delivered to a patient is important because an improper dose or the administration of the wrong drug can cause serious problems. A problem associated with peritoneal dialysis, for example, is an improperly mixed or non-mixed solution being delivered to a patient. Certain types of dialysate are packaged in dual-chamber bags, in which one chamber includes a buffer solution and the other chamber includes a concentrated glucose solution. The chambers of the bag are separated by a peelable or frangible seal that the patient or caregiver ruptures to open. The pH value of either the buffer solution and the glucose solution is such that the liquids alone are potentially harmful to the patient. The resulting pH value of the two fluids properly mixed however is suitable for injection into the patient's peritoneum. With peritoneal dialysis, therefore, it is desirable to make sure that the peelable or frangible seal is ruptured so that the resulting solution is mixed properly.

Certain dialysates, such as those used in hemodialysis, are bicarbonate-based. Bicarbonate is unstable in the presence of magnesium and calcium and forms a precipitate after a period of time. Accordingly, bicarbonate based dialysate needs to be packaged in a dual chamber supply container or bag. Here, premature mixing of the bicarbonate and contents of adjacent chambers may have deleterious effects on the resulting combination or render the combination of contents useless after an extended time. Bicarbonate alone can also be physiologically unsafe for the patient. Accordingly, it is necessary to properly mix the bicarbonate and other solution to form a final solution before contacting any solution with the patient's blood. With hemodialysis, therefore, it is desirable to make sure that solution has been mixed timely and properly.

Again, with any medical fluid injection, it is important to know that the proper type and dose of a drug or medical fluid is being infused into a patient.

SUMMARY

The present disclosure provides systems and apparatuses for sensing various electrical and thermal properties of a medical fluid, such as a drug or other medicament. The disclosure is described generally for a dialysis or renal failure therapy system having a need to know fluid conductivity, temperature, resistance, impedance, etc., however, the teachings herein are applicable to medical delivery systems and medical fluid delivery in general.

Generally, the systems involve the use of one or a pair of metal or conductive contacts placed in a fluid pathway, such as a disposable fluid pathway. Fluid pathways described herein include tubes, such as medical fluid supply tubes, drug infusion tubes, drain tubes, patient tubes, fluid heater tubes, etc. Other pathways include pathways defined by and occurring within a disposable fluid pumping/valving cassette. While the fluid pathways discussed herein are for the most part disposable (e.g., for handling sterile fluids), the pathways do not have to be disposable and, e.g., can be cleaned or sterilized between treatments.

The electrical contacts are used to sense a variety of fluid properties including conductivity sensing, needle or catheter access disconnection, temperature sensing, and valve leak detection. For conductivity sensing, a pair of electrodes is provided and a signal (e.g., current signal) is injected through the contacts and a fluid or hydraulic pathway in communication with the contacts. A resistance sensor measures a resistance of the fluid in the pathway between the contacts. A processor using one or more algorithm compensates for fluid temperature and calculates a conductivity using the sensed resistance. Solution conductivity sensitivity to temperature is approximately 2% per ° C.

Different fluids produce different sensed resistances, yielding different conductivities. With dialysate, for example, the inventors have found that conductivity can be used to sense between a dialysate buffer concentrate, a dialysate glucose concentrate and a mixed dialysate of buffer and glucose. Using the same apparatus and method, concentration can be used to detect whether a proper drug is about to be administered to the patient or whether a proper dose of the drug is about to be administered. Other detectable fluids include but are not limited to a parenteral compounding fluid, an intravenous infusion fluid and a chemotherapeutic compounding fluid.

The above sensing can be done using an absolute analysis, e.g., comparing the measured conductivity to an acceptable range of conductivities. Certain types of sensing can be done alternatively on a relative basis, for example, sensing whether multiple chamber bags have been opened properly. For example, multiple chamber supply bags can have integral tubing connectors as shown below. The connectors are filled initially with solution concentrate from the side of the container where the connector is attached. Mixing of solution from the other chamber into the connector chamber does not immediately affect the solution in the integral tube connector. Thus the sensed conductivity signal of fluid flowing from a properly mixed container will have a characteristic step change from that of the unmixed fluid in the tube connector to that of the mixed solution in the opened bag or container. Thus an unmixed or improperly mixed solution can be detected as the absence of detecting this step change in measured conductivity of the solution initially flowing from the container. This approach is advantageous in one respect because it does not necessitate an absolute concentration calibration and use of a lookup table. Instead, the approach looks for a change in conductivity.

For access disconnection, the electrodes can be used to sense a change in an electrical value of the medical fluid, e.g., dialysate. One preferred electrical value for access disconnection is impedance, although voltage or other values can be sensed alternatively. Likewise, these values can be used to check for a leaking valve. The metal electrodes also act as good thermal conductors for more accurate detection of fluid temperature.

Disclosed herein are various conductivity cells employing a pair of electrodes having varying geometries and surface areas with respect to the fluid path being sensed. The electrodes can be made of different materials and are integrated into a fluid tube or pumping cassette in a variety of ways. For example, the electrodes can be metal or of a conductive plastic. The electrodes are solvent bonded to the fluid pathway in one embodiment. In other embodiments, the electrodes are molded into the fluid pathway or sealed mechanically, e.g., via a retainer ring or threads. The surface area contact of the fluid and the electrodes can be controlled tightly by extending the electrodes entirely across the hydraulic pathway as opposed to partial insertion. However, an accurate apparatus for partial insertion is shown below.

The present disclosure also sets forth apparatus and associated electronics for interfacing with the conductivity cells, either integrated with tubing or a cassette.

It is therefore an advantage of the present disclosure to provide a multi-functional medical fluid or drug sensor, such as to detect proper dose, proper needle access, and valve leak detection.

It is another advantage of the present disclosure to provide an economical and efficient apparatus and method for incorporating conductive components into a tube or pumping cassette.

It is a further advantage of the present disclosure to provide an accurate apparatus and method for determining medical or drug fluid constituents.

It is yet a further advantage of the present disclosure to provide a system and method for measuring at least one of medical fluid resistance, conductivity and temperature.

It is yet another advantage of the present disclosure to provide apparatus and method for more accurately and safely controlling a renal failure therapy system.

Additional features and advantages are described herein, and will be apparent from, the following Detailed Description and the figures.

BRIEF DESCRIPTION OF THE FIGURES

FIGS. 3B and 3C are schematic views of alternative electrical systems which protect against and detect poor electrical connection between sensing electrodes and the dialysis instrument.

DETAILED DESCRIPTION

Figure 1:
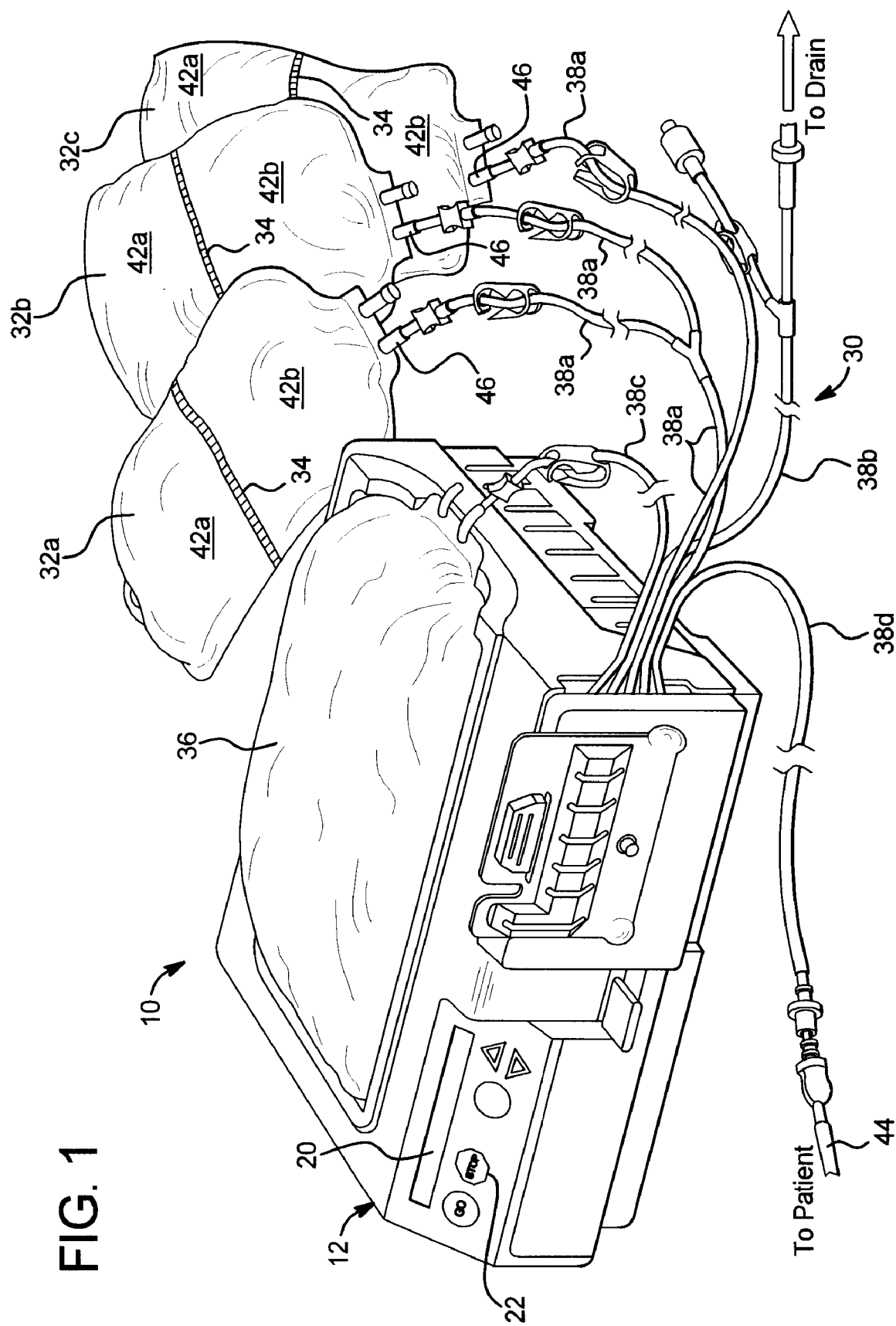
FIG. 1 is a perspective view of a renal failure therapy system employing a conductivity, resistance and/or temperature sensing system and method.

Referring now to the drawings and in particular to FIGS. 1, 3A, 3B and 3C, a renal failure therapy system 10 is provided. System 10 is applicable generally to include any type of renal failure therapy system, such as peritoneal dialysis ("PD"), hemodialysis ("HD"), hemofiltration ("HF"), hemodiafiltration ("HDF"), colorectal dialysis and continuous renal replacement therapy ("CRRT").

Figure 3A:
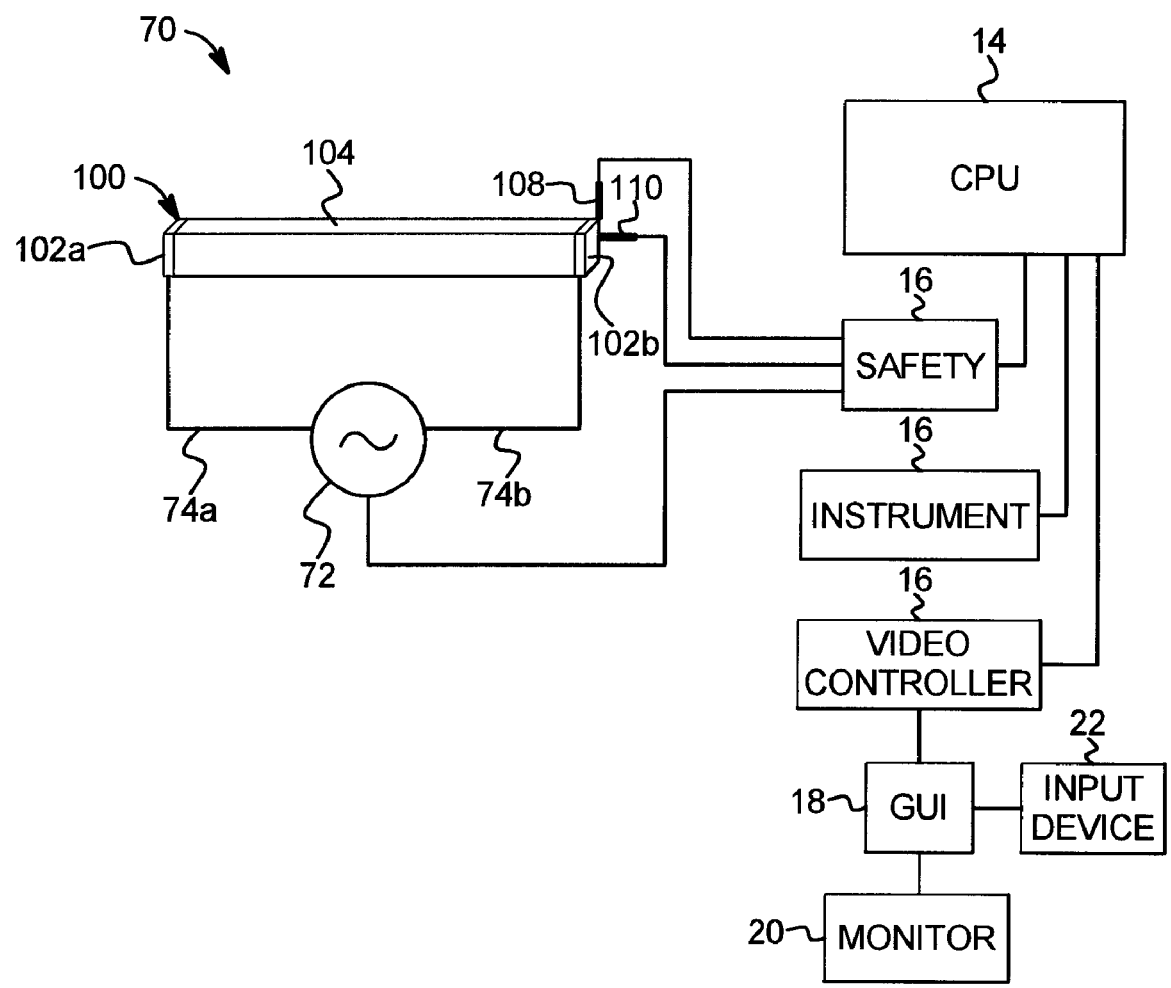
FIG. 3A is a schematic illustration of a conductivity cell and electrical schematic used for example with the renal failure therapy system of FIG. 1.

System 10 in the illustrated embodiment includes a dialysis instrument 12. Dialysis instrument 12 is configured for whichever type of renal failure therapy system is used. Dialysis instrument 12 as seen in FIG. 3A includes a central processing unit ("CPU") 14 and a plurality of controllers 16 operable with central processing unit 14. Central processing unit 14 also operates with a graphical user-machine interface ("GUI") 18, e.g., via a video controller 16, which includes a video monitor 20 and one or more type of input device 22, such as a touch screen or electromechanical input device (e.g., membrane switch see also FIG. 1).

Figure 2:
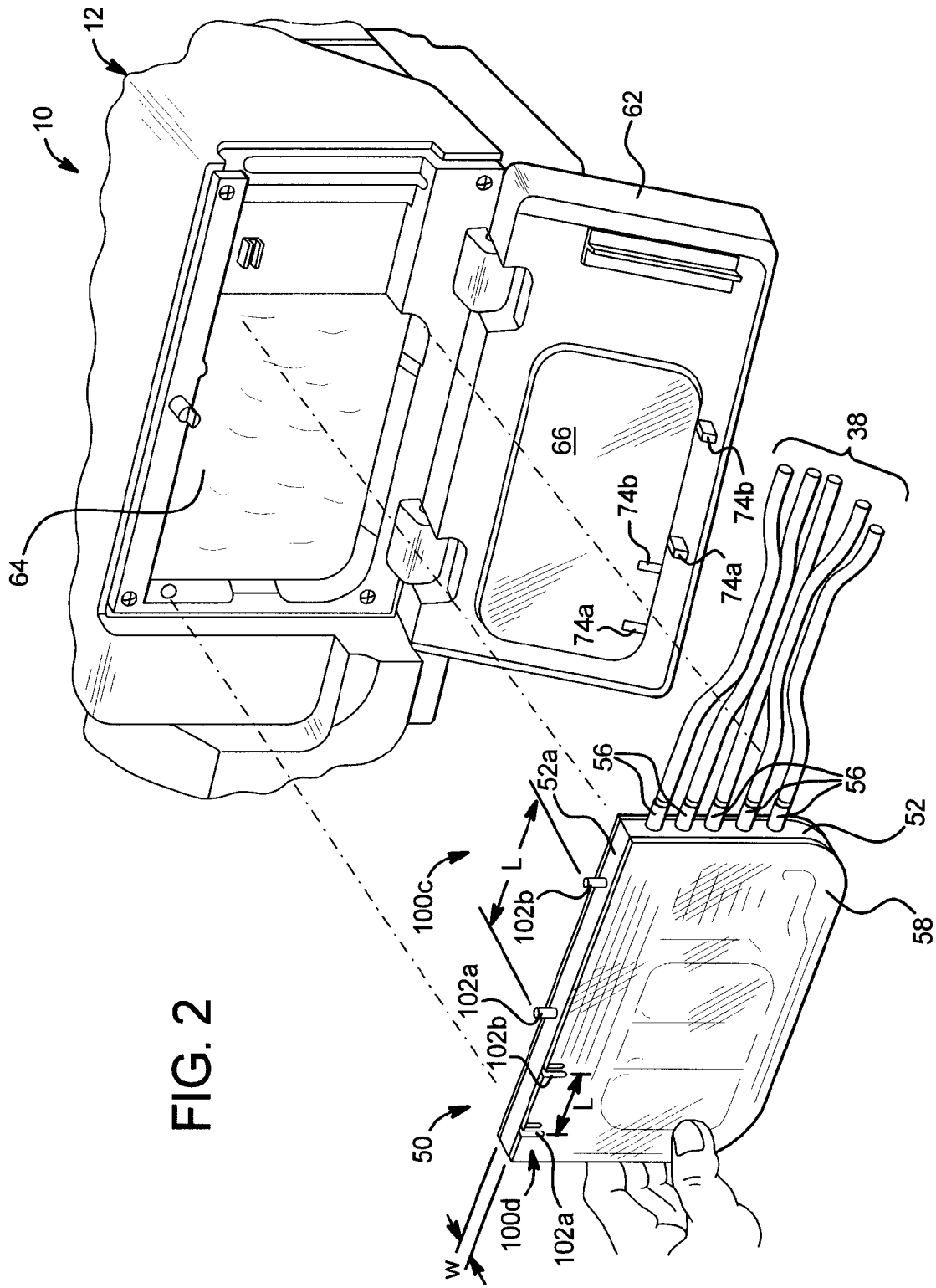
FIG. 2 is a perspective view of a disposable cassette employing conductive sensors and a machine operating with such cassette.

As seen in FIG. 1, dialysis instrument 12 accepts and operates with a disposable apparatus 30. Disposable apparatus 30 can include any one or more of supply bags 32a to 32c (referred to herein collectively as supply bags 32 or individually, generally as supply bag 32) shown here as dual or multi-chamber supply bags separating two fluids via a peel or frangible seal 34, drain bag (not illustrated), a warmer bag 36, bag tubes 38a to 38d (referred to herein collectively as tubing or tubes 38 or individually, generally as tube 38) and a disposable pumping/valve cassette 50 (FIG. 2). Depending on the type and structure of the renal failure therapy system 10, one or more of the items of disposable apparatus 30 may not be needed. For example, any system can pump spent fluid to a house drain, such as a toilet or sink, instead of to drain bag. System 10 can also include an inline heater, in which case warmer bag 36 is not needed.

While three supply bags 32 are shown, system 10 can employ any suitable number of supply bags. Supply bags 32 are shown having multiple chambers 42a and 42b, separated by frangible seal 34, which hold different solutions depending on the type of therapy employed. For example, chambers 42a and 42b can hold buffer and glucose for PD or acetate and bicarbonate solution for HD. Supply bags 32 are alternatively single chamber bags, which hold a single solution, such as lactate or acetate. Alternatively, multiple chamber bags with more than two chambers may be employed to deliver parenteral nutrition solutions for example.

Figure 12:
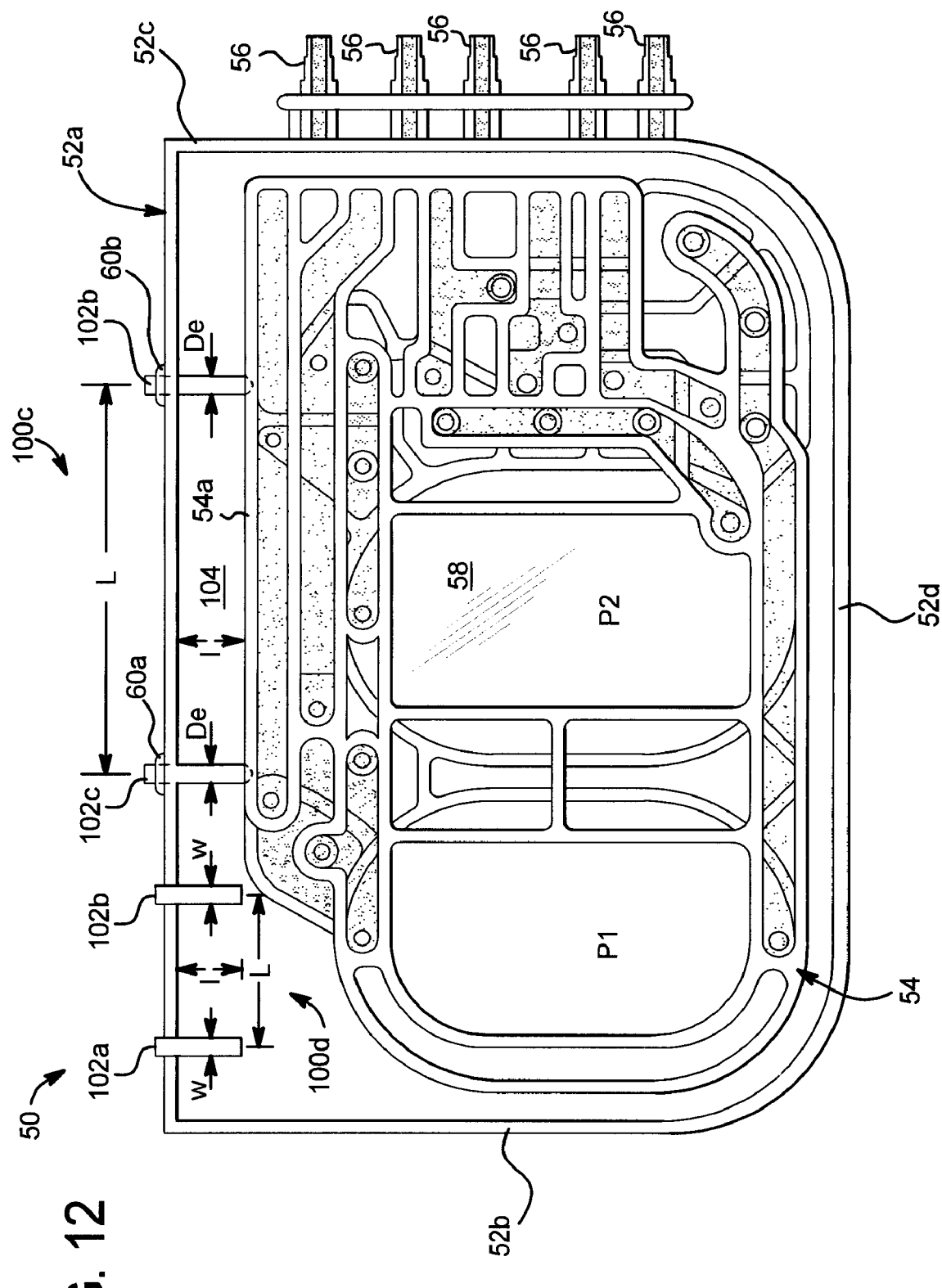
FIG. 12 is a side elevation view of a disposable cassette having an integrated conductivity cell.

One embodiment of a disposable cassette 50 is shown in more detail below in connection with FIG. 12. As seen in FIGS. 1 and 2, cassette 50 connects to supply bags 32, drain bag and warmer bag 36 via tubes 38a, 38b and 38c, respectively. Tube 38d runs to a patient connection 44. As shown in detail below, suitable places to place the conductivity cells of system 10 include different areas of tubing 38, e.g., in each of supply tubes 38a, in warmer bag tube 38c or patient tube 38d (could be two patient tubes, e.g., arterial and venous line, for hemodialysis). A conductivity cell can also be placed in cassette 50 as seen in FIGS. 12 to 15.

One primary reason for the conductivity cells described herein is to make sure that system 10 is delivering a proper solution or properly mixed solution to the patient, which in such case would make placing a conductivity cell in drain line 38b unlikely. However, an additional conductivity cell could be placed in drain line 38b, e.g., for diagnostic or therapy effectiveness purposes.

Placing the conductivity cell in solution lines 38a enables each supply bag 32 to be tested individually. Placing the conductivity cell in warmer bag tube 38c or patient tube 38d allows a single conductivity cell to ensure that proper fluid or properly mixed fluid is delivered to the patient. Likewise, placing the conductivity cell in the disposable cassette 50 enables a single conductivity cell to be used. Placement in cassette 50 has the added benefit that the cassette is already placed into operable contact with dialysis instrument 12 for operation. Placing the conductivity cell in tubing 38 in one embodiment requires that section of the tubing to be coupled operably to dialysis instrument 12. It is contemplated however to provide a separate instrument or hardware device (see, e.g., hardware unit 112 of FIG. 6), which operates with a conductivity cell located in one of tubes 38.

Referring now to FIG. 3A, an electrical scheme 70 for a conductivity cell 100 (and other functions) is illustrated. The circuitry and processing for the electrical schematic 70 in one embodiment is placed on a printed circuit board ("PCB"), e.g., on one of controllers 16 or CPU 14. The electronics includes a voltage or current source 72, which for example is placed on safety controller 16. Source 72 generates an electrical signal, which travels along lead or trace 74a, to one electrode 102a of cell 100, through a hydraulic or liquid pathway 104 of cell 100, through a return electrode 102b, return lead or trace 74b, returning to source 72. Frequency of the generated electrical signal is maintained at a desired level as seen below in connection with FIG. 9.

Liquid pathway 104 interacts with a plurality of sensors, such as an electrical, e.g., voltage or resistance sensor 108 and/or a temperature sensor 110. Electrical or resistance sensor 108 can be a current or voltage sensor, which in combination with a known driving voltage or current, respectively, allows for a calculation of resistance and conductivity. Resistance sensor 108 is used in a conductivity calculation as described in detail below. Temperature sensor 110 can be of a type such as a diode, thermistor, integrated circuit sensor, infrared sensor, or resistance temperature device ("RTD").

Electrical sensor 108 can also be used to detect a patient access disconnection. One suitable access disconnection system ("ADS") is disclosed in copending patent application entitled, "Enhanced Signal Detection For Access Disconnection Systems", filed Feb. 16, 2007, Ser. No. 11/676,110, assigned to the eventual assignee of the present disclosure ("The '110 application"). The referenced application discloses at least one embodiment that looks for a change in impedance occurring in the dialysate path. Hydraulic or liquid pathway 104 can thus be part of the dialysate path. The referenced application also discloses at least one embodiment that looks for a change in impedance occurring in a blood path. Hydraulic or liquid circuit 104 can also therefore be part of the blood path.

Temperature sensor 110 senses a temperature of the medical fluid, e.g., dialysate, and takes advantage of the invasive metal electrodes 102a and 102b (referred to herein collectively as electrodes 102 or individually, generally as electrode 102). Knowing the temperature of the fluid is useful for fluid heating, patient safety, and perhaps pumping accuracy, e.g., for a volumetric system based on Boyle's Law. As seen, electrodes 102 can be multifunctional, which is true in any of the embodiments or configurations described below.

The signals from sensors 108 and 110 can be sent through a series of components (not illustrated), e.g., located on one of the controllers 16, such as: (i) a filter or filters, which can act to filter noise from the signal, e.g., noise derived from the rotation from a blood pump to minimize a false negative and/or positive detection of needle dislodgment; (ii) a rectifier; (iii) a peak detector; and/or (iv) an analog to digital converter ("ADC") to digitize the signal. Controller 16 (referring to one of the controllers of FIG. 3) or CPU 14 includes a memory that stores the digital signal, e.g., in a buffer, for processing by a processor, such as a digital signal processor ("DSP"), which can be located at controller 16 or CPU 14.

Controller 16 or CPU 14 continuously measures the electrical, e.g., voltage signal and processes the signal over time. The processor in one embodiment compares the digitized signals to look for changes over time and/or to compare the signals with a baseline or set point. For ADS, for example, signals are compared to an expected or baseline signal. Controller 16 or CPU 14 continually performs a calculation to determine whether a difference in the sensed signal compared to an expected or baseline signal is large enough to constitute a needle dislodgement. Variations in treatment can cause the expected or baseline signal to drift. System 10 can account for this.

For conductivity sensing, the signals in one embodiment are compared to an absolute norm, e.g., a range of values stored in a database or lookup table in the memory of controller 16 or CPU 14. If the conductivity falls within a safe range of conductivities, the dialysate is assumed to be mixed properly. Otherwise an alarm condition is reached as discussed below.

If electrical scheme 70 of system 10 senses an access disconnection or a conductivity of medical fluid or dialysate that is out of range, system 10 takes evasive action to ensure the safety of the patient. With ADS, the goal is to minimize blood loss from the patient. In an embodiment, safety controller 16 receiving the signals from sensors 108 and 110 sends an error message to CPU 14, which in turn sends a command to an instrument controller 16 to cause instrument 12 to take one or more evasive action, such as to shut down a pump, occlude a line 38 or close a valve (and corresponding fluid pathway) of cassette 50.

In an alarm state, CPU 14 in one embodiment also sends a command to GUI controller 16. GUI controller causes GUI 18 to display a message, such as an error and/or instructional message, on video monitor 20. Although not illustrated, instrument 12 can be equipped with speakers and sound or voice activation to sound an alarm or verbalize an alarm and/or corrective action. The visual or audible alarm alerts the patient, a medical care provider (e.g., doctor or registered nurse) or a non-medical care provider (e.g., family member or friend) of the conductivity error or needle dislodgment.

For ADS, the alarm function is particularly useful during dialysis therapy in a non-medical facility, such as in a home setting or self-care setting in which dialysis therapy is administered typically by the patient and/or a non-medical care provider in a non-medical setting or environment. The ADS alarms the patient or caregiver to ensure that the dialysis therapy has been terminated by, for example, checking that the blood pump has been automatically shut off to minimize blood loss to the patient.

For a conductivity error, the alarm can alert the patient or caregiver to check that peel seals 34 of dual chamber bags 32 have been opened. Instrument 12 of system 10 halts pumping and/or occludes one or more appropriate tubes 38 or fluid paths of cassette 50 and also causes any improperly mixed fluid to be dumped to drain. Once fluid of the correct conductivity is sensed, treatment can continue.

For a conductivity error in an infusion pump setting, the alarm can tell the hospital nurse or machine operator to check that the correct solution or solution having the correct dose of a medicament has been connected to the instrument 12.

The communication between electrical scheme 70 and instrument 12 can be either hard-wired, for example if electrical scheme 70 is provided with instrument 12. Alternatively, the communication is a wireless communication (e.g., wireless RF interface). For example if electrical scheme 70 is provided in a separate unit or housing (see, e.g., unit 112 of FIG. 6), the separate unit can communicate wirelessly with instrument 12. With a wireless interface, the separate unit can implement scheme 70 and have its own controller with memory, processing, power supply, etc., mentioned above. Additionally, the unit can include a transceiver for two-way communication with a transceiver located within instrument 12.

Referring still to FIG. 3A, the operation of cell 100 as a conductivity sensor is described. Here, system 70 uses an electrical signal, e.g., current, between spaced-apart electrodes 102a and 102b to test the quality of a medical fluid to be delivered to a patient, e.g., in a renal failure therapy setting or drug infusion setting. Electrodes 102 are disposed within the flow path 104 of the medical fluid so as to contact the medical fluid.

Assuming flow path 104 to have a length L and cross-sectional hydraulic area $A_h$, assuming the dialysate or drug to be an isotropic, homogeneous material, and assuming that signal source applies a signal having a current i at a voltage V, then the conductivity of the isotropic, homogeneous material can be expressed as:

$$\sigma = (L * i)/(V * A_h),$$

which can be expressed in units of mS/cm. The geometry of cell 100 of FIG. 3A, in which the entire cross-sectional hydraulic area $A_h$ contacts or is contacted by an electrode 102, simplifies conductivity measuring but is problematic to a flow-through system. Some of the hydraulic area $A_h$ needs to be uncovered or not contacted by an electrode 102 to allow fluid to flow past the electrode. In such a case, a cell constant k is added to the equation to account for the specific geometry of: (i) hydraulic area $A_h$, (ii) the contact area and shape of the electrode 102, and (iii) the relation of (i) to (ii). The conductivity of the isotropic, homogeneous material in the flow-through system is now expressed as:

$$\sigma = (k * L * i)/(V * A_h),$$

FIGS. 3B and 3C illustrate alternative electrical systems 170 and 270, respectively. Systems 170 and 270 include CPU 14, controllers 16, GUI 18, monitor 20 and input devices 22 as shown and described above with system 70 of FIG. 3A. Accordingly these apparatuses are not shown in these additional figures. The primary difference with systems 170 and 270 versus system 70 involves the addition of redundant contacts and sensing, which ensure proper performance regardless of or provides a detection of a faulty or improperly made electrical contact between at least electrodes 102 and the instrument or machine 12. Systems 170 and 270 mitigate a contact failure mode that may not be detectable with system 70.

System 170 shows dual contacts on each electrode 102a and 102b that compensate for a poor electrical connection between the instrument 12 (FIGS. 1 and 2) and either electrode 102. As shown, system 170 includes a signal source 72 applying a known signal, e.g., voltage signal, to contacts 102a and 102b. Sensor 108 is shown here as a current meter, which measures the current flowing from signal source 72 to conductivity cell 100. The secondary contact at each electrode 102a and 102b communicates with a voltage meter 172, which measures the actual voltage applied to the electrodes 102. The ratio of the measured current to measured voltage, and other system constants, are used to determine the conductivity of the fluid between the electrodes.

All of the current measured through electrodes 102 supplied from signal source 72 must be applied through the fluid because there is no other path that the current can take between the electrodes. If there is a relatively poor electrical contact between the signal source and the electrode, however, the voltage applied to electrodes 102 decreases, while the current supplied through electrodes 102 remains within normal specifications. If voltage meter 172 measures a voltage at the electrodes 102 that is outside a normal operating voltage due to an inadequate electrical contact between signal source 72 and electrodes 102, the electronics within instrument 12 detects the voltage as being out of specification and signals a faulty cassette or cell loading alarm. Instrument 12 can confirm such condition by detecting a large difference between the voltage that signal source 72 applies versus the voltage that voltage meter 172 measures.

System 270 shows another alternative embodiment in FIG. 3C. System 270 includes signal source 72, current meter 108 (for conductivity determination) and voltage meter 172 discussed above with system 170. System 270 additionally measures a contact resistance between conductivity cell 100 and instrument 12.

Switches S1 and S2 connect an ohmmeter 272 to electrodes 102a and 102b, respectively, for example in a multiplexed fashion at the beginning of therapy to interrogate the electrical connection at each electrode 102a and 102b separately. Ohmmeter 272 measures a total resistance between electrodes 102 and the electronic circuits contained within instrument 12. After the resistance is determined to be within an allowable tolerance, switches S1 and S2 connect the electrodes 102 to signal source 72 and voltage meter 172. It should be noted that system 270 can connect signal source 72 and voltage meter 172 to each other within instrument 12 so that the signal source and voltage meter do not need to be connected separately at electrodes 102 as shown in FIG. 3C.

Figure 4:
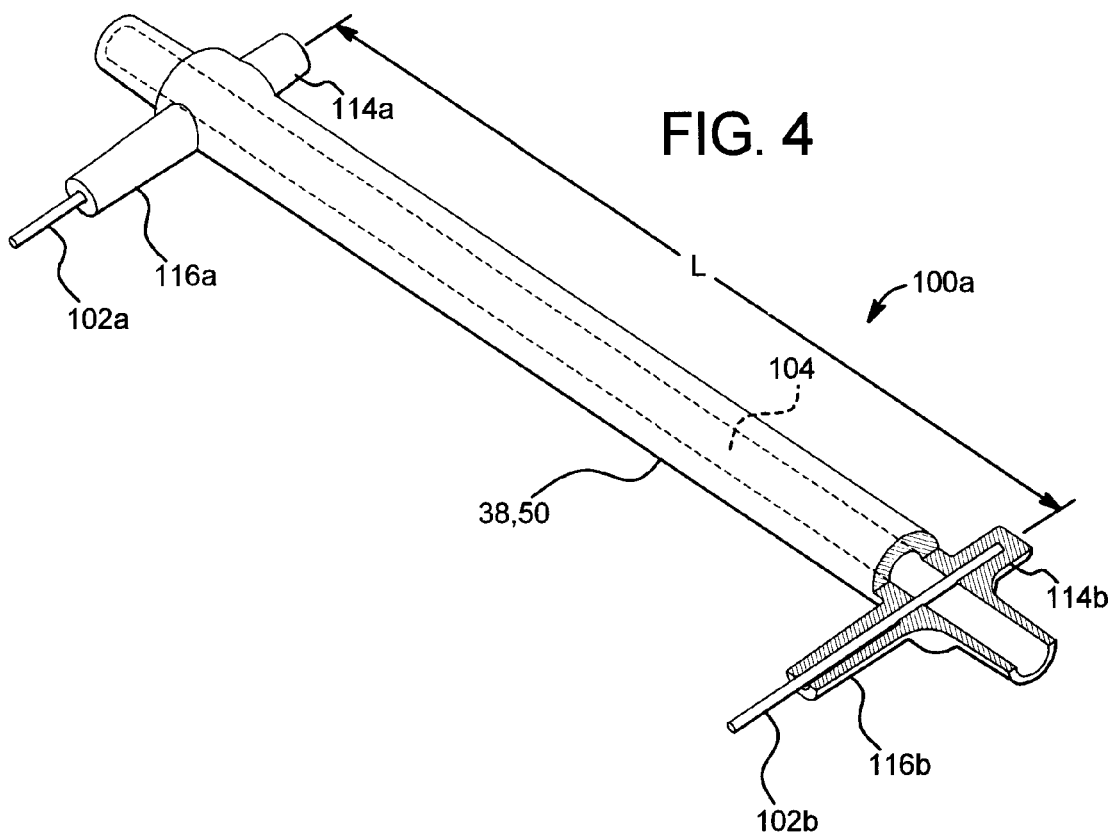
FIGS. 4 and 5 are perspective views of a tubing based conductivity cell using metal electrodes.
Figure 5:
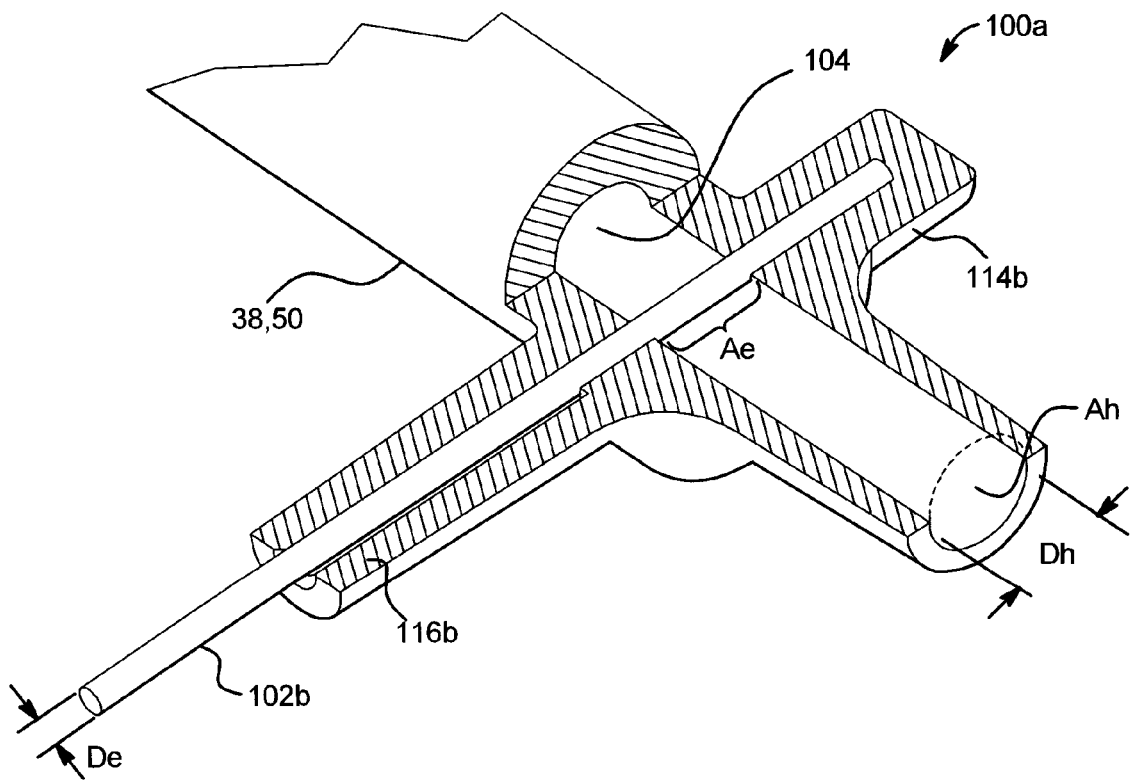
Figure 6:
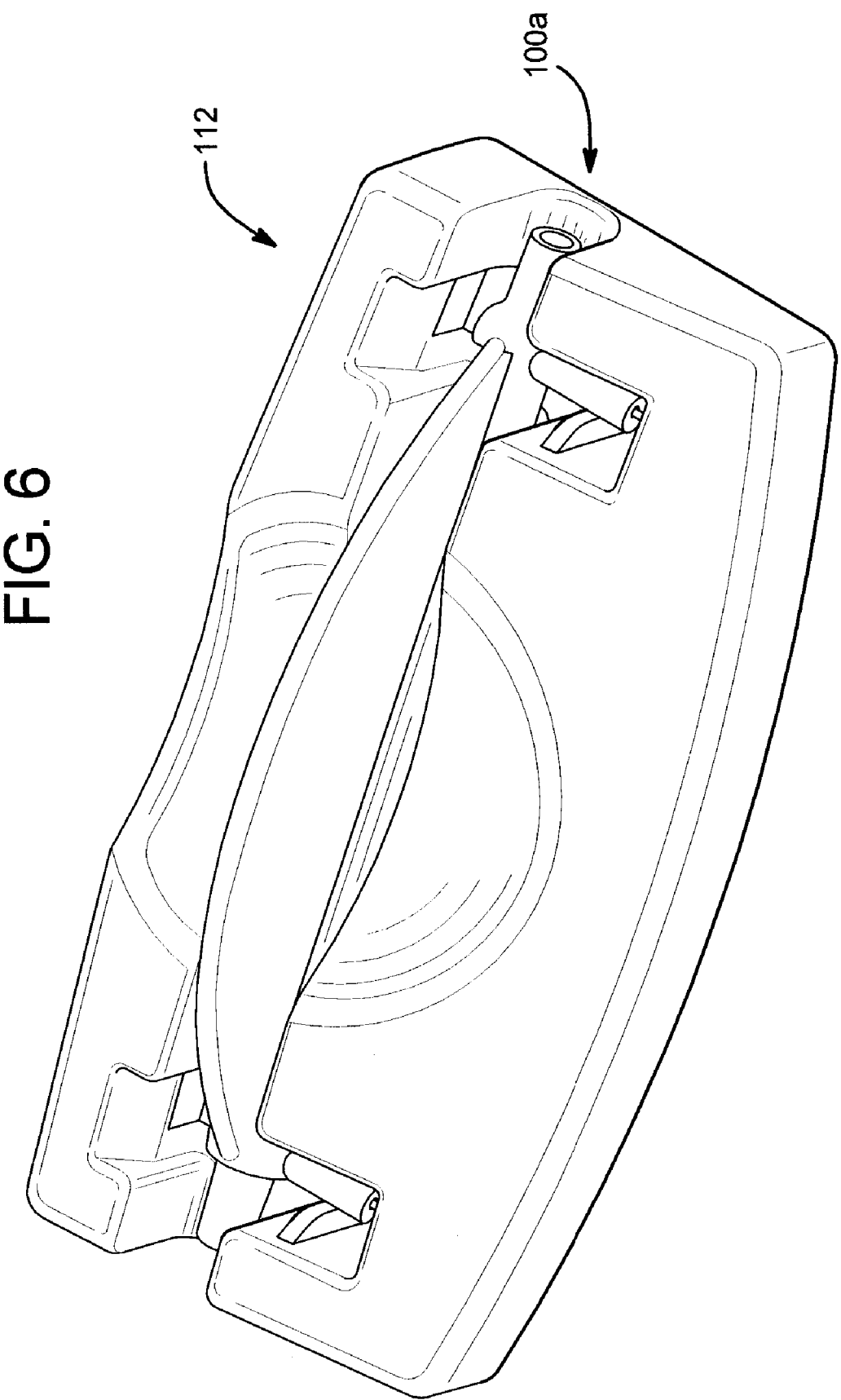
FIG. 6 is a perspective view illustrating one embodiment of a stand-alone hardware unit configured to hold the tubing based conductivity cell of FIGS. 3A, 3B, 3C and 4 for proper operation.

Referring now to FIGS. 4 to 6, cell 100a illustrates one suitable flow-through conductivity cell. The electrodes of cell 100a can be used alternatively or additionally for any of the types of sensing discussed herein, e.g., needle/catheter access disconnection, valve leak detection, and temperature sensing. For ease of illustration, the tube or conduit of cell 100a is labeled conduit 38, 50, which signifies that cell 100a can be part of different fluid flow structures, such as cassette 50, one of tubes 38 as discussed above, a supply bag 32 or other container, a tube of an infusion pump or any type of relatively non-conductive fluid conduit, be it disposable or non-disposable. Cell 100a can interface directly with instrument 12 or with a separate hardware unit 112 shown in FIG. 6.

Cell 100a transmits a current through a medical fluid, e.g., dialysate, flowing within conduit 38, 50 between a pair of opposing electrodes 102a and 102b. Instrument 12 or separate hardware unit 112 includes circuitry 70 shown in FIG. 3A, which controls the transmission of the electrical current between the electrodes 102 and measures the resistance of the medical fluid.

In one embodiment, conduit 38, 50 is injection molded plastic. Here, conduit 38, 50 is injection molded around and sealed to electrodes 102. In another embodiment, conduit 38, 50 is extruded plastic. In still a further embodiment, electrodes 102 are bonded adhesively to conduit 38, 50. In yet another embodiment, electrodes 102 are inserted into conduit 38, 50 via an insert molding process. Conduit 38, 50 can accordingly be made of moldable material, which is chemically and biologically inert with respect to the medical fluids, e.g., dialysate or drugs, and is electrically insulative in an embodiment. Suitable materials for conduit 38, 50 include acrylonitrile butadiene styrene ("ABS"), polyvinyl chloride ("PVC"), silicone rubber, polyolefin, cyclic olefin and cyclic olefin copolymers ("COC"), polycarbonates, synthetic and natural rubber, thermoplastic elastomers, glass, silicone and other semiconductors used in micro electro-mechanical ("MEMS") fabrication processes.

Electrodes 102 are stainless steel in one embodiment, which is generally considered as a safe metal for contacting a medical fluid. Electrodes 102a and 102b can alternatively be formed of different materials, perhaps for better electrical or thermal properties, so to provide a thermocouple effect for measuring the temperature of the medical fluid, and/or in a non-sterile situation or for example, sensing effluent or spent fluid (that has already contacted the patient) electrodes can alternatively be made of a conductive plastic described in more detail below. Suitable conductive plastics are described in the '110 application referenced and incorporated above.

Electrodes 102a and 102b of cell 100a are illustrated as being cylindrical but could alternatively be square, rectangular or of an arbitrary cross-section. Electrodes 102 extend into or through fluid pathway 104 in an at least substantially perpendicular orientation relative to the flow axis through the pathway. Alternatively, electrodes may extend along the fluid pathway, e.g., as surface-printed electrodes (discussed below) having a controlled separation distance. It is important to know the amount of surface area of electrodes 102 that the medical fluid contacts accurately so that the conductivity can be calculated accurately. Accordingly, conduit 38, 50 includes or provides pockets 114a and 114b (referred to herein collectively as pockets 114 or generally, individually as pocket 114) that receive electrodes 102a and 102b, respectively. In this relatively easily controlled way, it is assured that electrodes 102 extend all the way across fluid pathway 104. Conduit 38, 50 also includes or provides posts 116a and 116b (referred to herein collectively as posts 116 or generally, individually as post 116), which hold electrodes 102a and 102b, respectively, firmly and in the proper at least substantially perpendicular orientation with respect to the flow of medical fluid through pathway 104. Extensions 116 also provide additional contact area for electrodes 102 to be sealed within conduit 38, 50 of cell 100a.

As discussed above, electrodes 102 can be adhesively joined to cell 100a. Here, the adhesive can be applied within posts 116, such that an adequate amount of adhesive is applied, but wherein the adhesive is kept safely away from fluid pathway 104. The plastic to metal adhesive process is readily amenable to high-volume production. The process can include forming molded, e.g., insert molded posts 116, inserting, e.g., stainless steel, electrodes or cannula needles 102, applying a metered adhesive (e.g., Loctite™ adhesive) and cross-linking the adhesive and material of plastic post 116 (e.g., ABS) for example with ultraviolet ("UV") light.

Parameters needing to be tightly controlled during high-volume manufacturing include fluid path length L, electrode size and surface characteristics, and hydraulic area $A_h$. An alternating current ("AC") signal, as either a driving current (i) or driving voltage (V), is used in one embodiment to preclude anodic loss of the electrodes. A direct current is not ideal because it would result in anodic erosion of one electrode, altered sensor calibration and create contaminates in the medical fluid. Resistance as has been discussed is determined by controlling the driving current (i) or voltage (V), measuring the other and calculating resistance.

As alluded to above, cell constant k for full contact electrodes 102 of FIG. 3A is unity. For an, e.g., circular fluid path 104 (of conduit 38, 50) of hydraulic diameter $D_h$ that the cylindrical and non-full contact area electrodes 102 of diameter $D_e$ of cell 100a of FIGS. 4 and 5 traverses, the electrode to solution contact area can be expressed as:

$$A_e \approx \pi * D_h * D_e$$

The cell constant k for cell 100a is then derived using the value of $A_e$ and hydraulic area $A_h$ diameter Db of electrode 102 of cell 100a. Assuming manufacturing variances $A'_e$, $A'_h$, and L' associated with parameters $A_e$, $A_h$, and L, respectively, the effects of the variances can be mitigated via making cell 100a with path length L relatively long so that resistance is high and the variance L' is a small percentage of L and at the same time imposing that the relative variance, L'/L, is the dominant variance, and $$L'/L >> A'_e/A_e, \text{ and } L'/L >> A'_h/A_h$$

Controlling L'/L ensures measurement accuracy and minimizes uncertainty without requiring overly stringent manufacturing controls of cross-sectional flow path area or electrode area. The electrode variance may be minimized by making the electrode surface area, $A_e$, larger than the hydraulic area, $A_h$.

In one experiment cells 100a as shown in FIGS. 4 and 5 were made having electrodes of stainless steel and having a diameter $D_e$ of 0.076 cm and a fluid pathway 104 of area $A_h$=0.11 $cm^2$. Electrodes 102a and 102b were spaced apart a hydraulic pathway distance (center to center) of 7.62 cm. Mixed dialysate solution was measured to have a resistance of about 15,210 ohms. Cell 100a and associated electronics 70 were able to distinguish mixed solution from unmixed solution. In particular, unmixed buffer was detected with a resistance of about 7,700 ohms, while glucose concentrate was detected with a resistance of about 177,000 ohms. Thus, circuitry 70 and cell 100a have a sensitivity of about 10 ohms or less when expecting to see a mixture of about 10,000 ohm resistance. For a solution which is expected to have a conductivity of about 12.3 mS/cm, this corresponds to a sensitivity of about 0.01 mS/cm.

Figure 7:
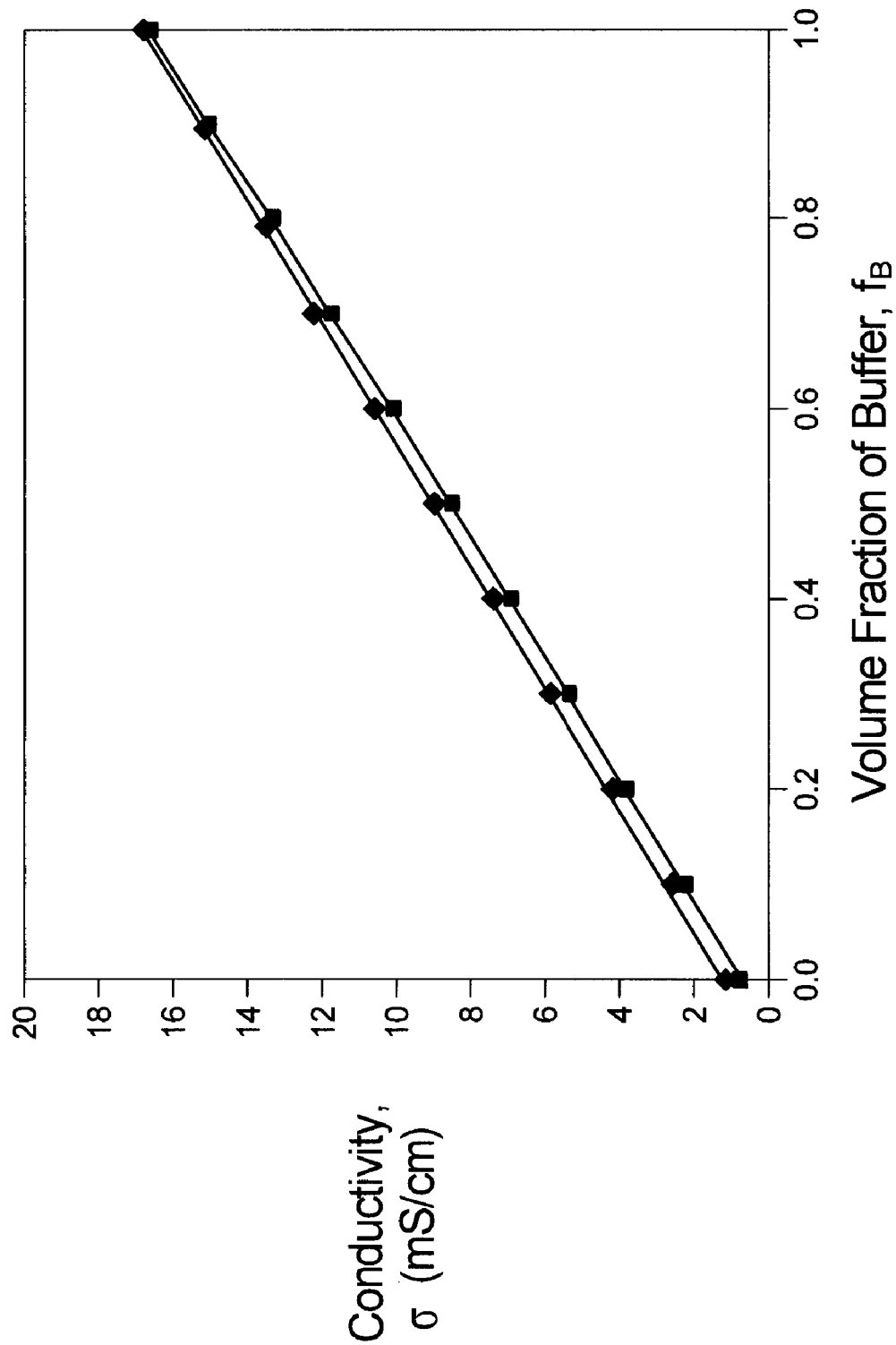
FIG. 7 is a graph illustrating a relationship between conductivity and a volume fraction of bicarbonate buffer in an buffer/glucose dialysate solution.
Figure 8:
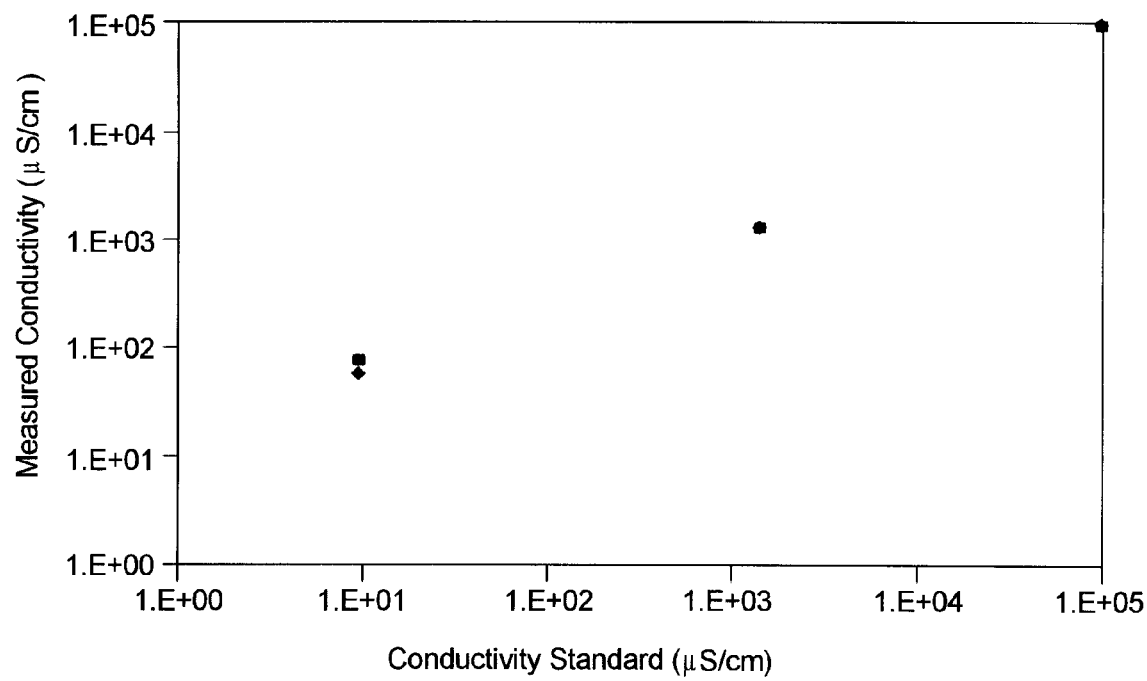
FIG. 8 is a graph showing cell calibration with conductivity standards.
Figure 9:
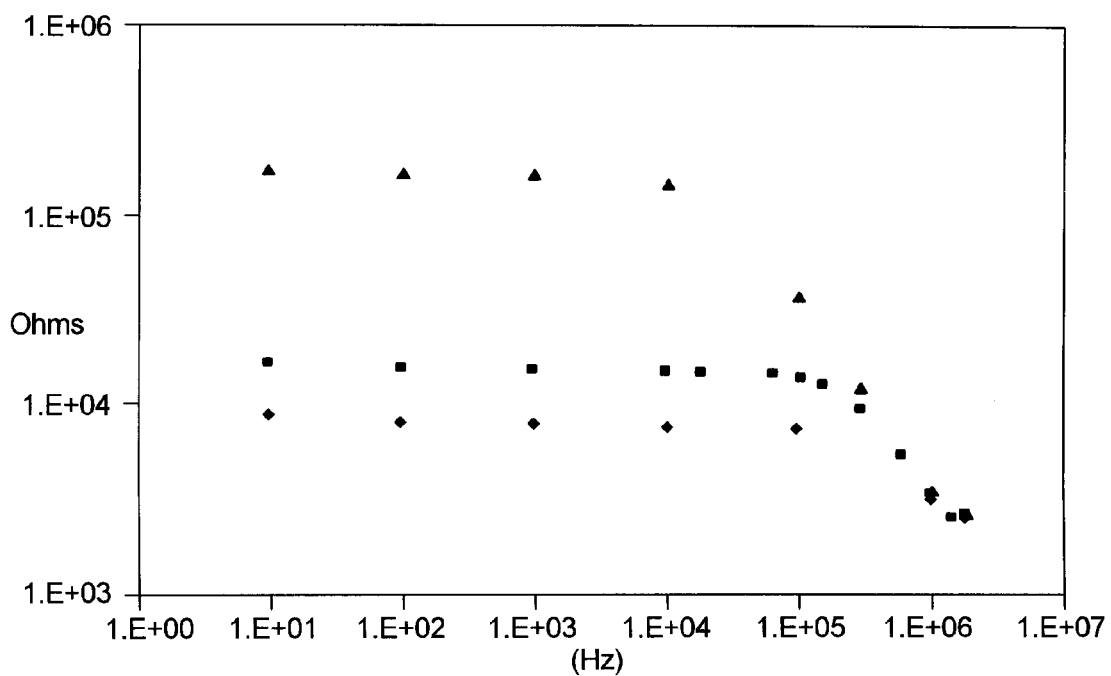
FIG. 9 is a graph showing measured conductivity versus frequency.

Results from testing have been tabulated in FIGS. 7 to 9. FIG. 7 shows a linear relationship of conductivity with varying volume fraction of bicarbonate buffer in a dialysis solution. Here, conductivity is a function of mix ratio. As the percentage of buffer, $f_B$ increases, so does conductivity. Diamonds in FIG. 7 represent 1.36 percent glucose dialysate. Squares in FIG. 7 represent 3.86 percent glucose dialysate. The dialysate of FIG. 7 is for a two-part dialysis solution, a buffered concentrate and a glucose concentrate. When mixed properly (e.g., $f_B$=0.63) the components combine to form a therapeutic solution with physiologic balance of pH, osmolarity, Na, for example. FIG. 8 shows cell calibration with different conductivity standards. Here, squares and diamonds represent replicated trials. In five cells of the same type, a coefficient of variation of about 1.4% in conductivities was measured. Thus, cell 100a and circuitry 70 were found to be relatively repeatable.

Modulating frequency provides an alternative method for distinguishing solution mix concentration. FIG. 9 illustrates the dependence of resistance (more generally impedance) or conductivity on signal frequency. As seen, the resistances are more distinct at lower signal frequencies (glucose concentrate in triangles, bicarbonate concentrate in diamonds and mixed solution in squares). When a certain signal frequency is reached, measured resistances begin to decrease. Therefore, in one embodiment signal frequency is maintained at a suitably low level, such as between about 10 to 100,000 Hz, e.g., at about 1000 Hz and solutions may be distinguished as differences in resistance measured. Alternatively, solutions may be distinguished by the frequency at which the resistance decreases, e.g., about 10,000 Hz for the glucose concentrate, about 100,000 Hz for the mixed solution and about 500,000 Hz for the buffer solution.

Once the resistance of the medical fluid is measured, a processor (e.g., located at CPU 14 or controller 16) applies an algorithm to the measured resistance, which compensates for temperature to calculate the conductivity of the medical fluid. The processor performs a matching check to compare the calculated conductivity of the medical fluid with, e.g., a lookup table in a database for the particular pharmaceutical substance to determine if the concentration of the pharmaceutical substance within the medical fluid is within an acceptable range. Detectable conditions for dialysis include, for example: (i) no disposable cell loaded (alarm); (ii) disposable cell loaded (no alarm); (iii) only glucose concentration detected (alarm); (iv) only bicarbonate concentration detected (alarm); and (v) mixed solution detected (no alarm).

If the measured concentration of the pharmaceutical substance is outside an acceptable range, the processor outputs a signal (e.g., from safety controller 16 to CPU 14 of the dialysis, infusion or other medication delivery system 10) to provide an alarm to the user and/or prevent the medication delivery system from delivering the medical fluid (e.g., by shutting down a pump, tube 38 or pathway of cassette 50). If the measured concentration of the pharmaceutical substance is within an acceptable range, the processor outputs a signal to proceed with the delivery of the medical fluid. In the case of APD, fluid mixing quality can be tested once (for each bag 32) before the start of therapy or during therapy to ensure proper mixing. Other detectable fluids include but are not limited to a parenteral compounding fluid, an intravenous infusion fluid and a chemotherapeutic compounding fluid.

In an alternative embodiment, detection is performed on a relative rather than an absolute basis. Here, instead of comparing a measured value to an acceptable range, cell 100 looks for a step change or relative change in conductivity. Here, a lookup table or absolute comparison is not needed. One example of this embodiment is possible in connection with dual chamber bag 32 having chambers 42a and 42b separated by a frangible seal 34. Dual chamber bags 32 in the illustrated embodiment have integral tubing/connectors 46 in communication with chambers 42b. While tubing 46 is shown as being a relatively short run in FIG. 1, integral tubing 46 can alternatively be longer and in one embodiment extend all the way to and connect directly to cassette 50. Tubing/connectors 46 are filled initially with solution concentrate from chamber 42b. Mixing of solution from the other chamber 42a into the connector chamber 42b once seal 34 is broken does not immediately affect the solution conductivity in tubing/connector 46, especially in longer lengths of tubing 46. Electrodes 102 positioned here along each of tubes 46 will therefore initially sense pure (or near pure) solution of chamber 42b flowing from bag 32, after which properly mixed fluid flows past electrodes 102 and causes a characteristic step change in conductivity. If solutions from chambers 42a and 42b are not mixed properly, the expected step change in conductivity does not occur, indicating that the chambers have not been mixed. This relative approach is advantageous in one respect because it does not necessitate an absolute calibration and use of a lookup table.

Referring again to FIG. 6, hardware unit 112 illustrates an embodiment of a separate testing mechanism or hardware unit including circuitry 70 which is, configured to apply an electrical signal and to measure the resistance of a medical fluid through a cell such as cell 100a. While separate hardware unit 112 is shown in operation with cell 100a, it should be appreciated that the hardware unit is alternatively operable with any of the cells discussed herein. Hardware unit 112 maintains the cell in a secured position and includes leads or contacts that contact each of the electrodes 102 of the cell to enable the cell to communicate electrically with the rest of circuit 70. A snap-fit is provided in one embodiment to provide enough force to minimize contact resistance but still allow the cell to be loaded and unloaded in an efficient and ergonomic manner. Hardware unit 112 can include a processor and hard-wired or wireless communication equipment as discussed herein.

Figure 10:
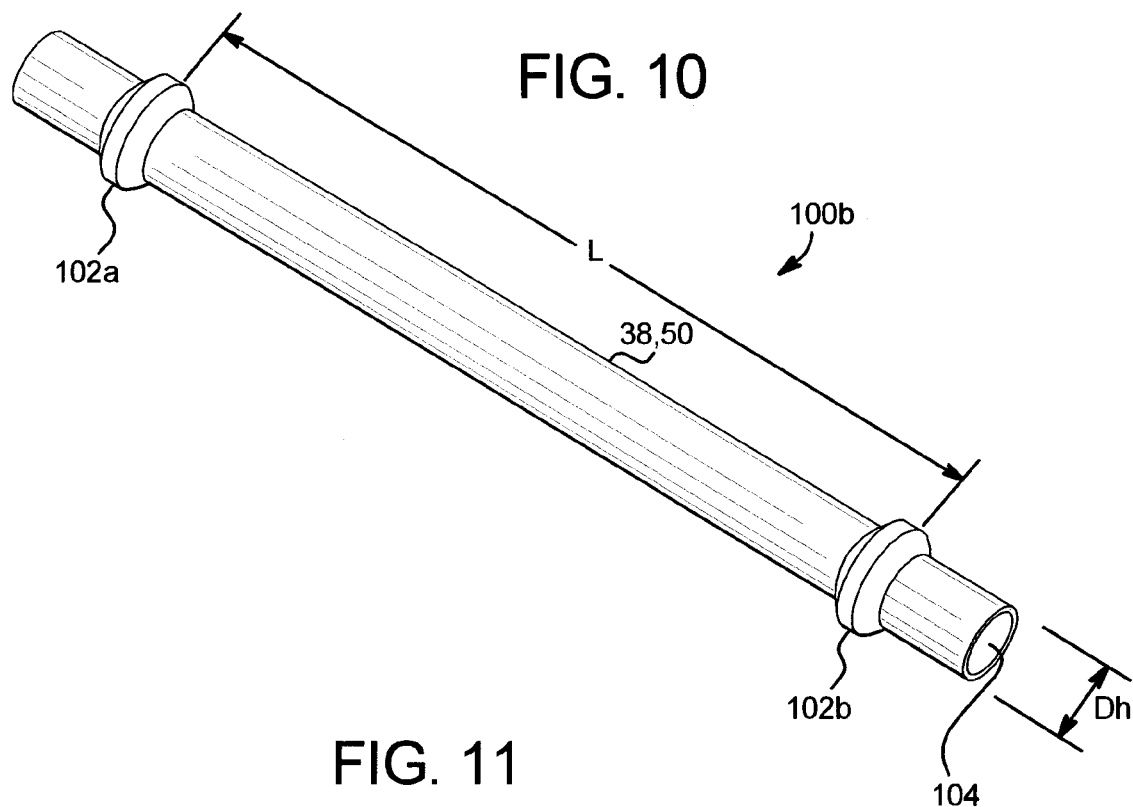
FIGS. 10 and 11 are perspective views of a tubing based conductivity cell using conductive plastic electrodes.
Figure 11:
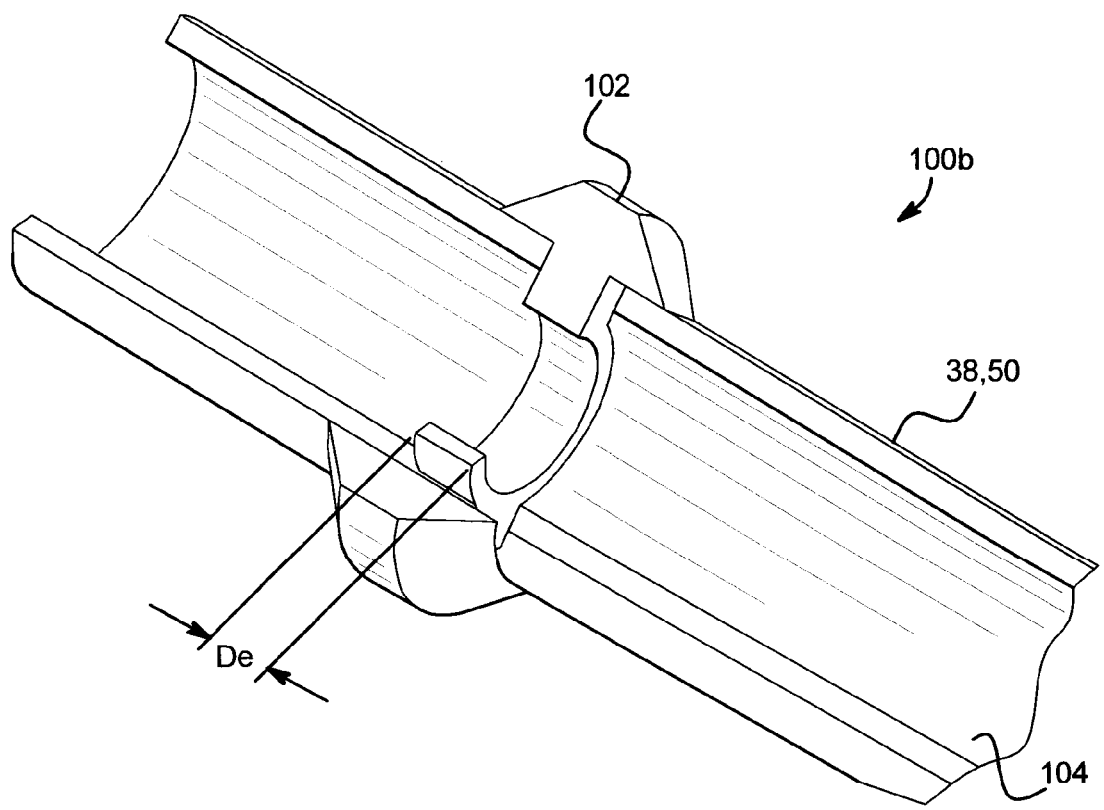

Referring now to FIGS. 10 and 11, cell 100b illustrates another embodiment for a conductivity, ADS, leak detection and/or heat sensor. Cell 100b again includes a pair of electrodes 102a and 102b, which in one embodiment are overmolded around a section of conduit 38, 50 defining hydraulic pathway 104 of hydraulic diameter $D_h$, having hydraulic Area $A_h$, and length L as described above. In one embodiment, cell 100b is formed using various sections of conduit 38, 50, which are inserted into a mold such that adjacent ends of the conduits are spaced apart. Then, an electrically conductive material, such as an electrically conductive plastic referenced above, is overmolded around adjacent ends of the conduit 38, 50. The space between the adjacent ends of the tubes 104 is filled with the conductive material, such that the conductive plastic forms a portion of the surface of the fluid passageway 104 of the cell 100b as seen best in FIG. 11. The exposed portions of the conductive material within the passageway 104 form the electrodes 102 that are in fluid communication with the medical fluid that flows through the passageway 104. The exposed portions can have a flat, cylindrical surface defining an annular surface area $A_e = \pi * D_e * \text{length} \, l_e$ of contact ring. Alternatively, exposed portions of conductive electrodes 102 can include inwardly facing surface area increasing apparatuses or members. In any case, the overmolding process connects adjacent tubes and provides a seal therebetween to form a continuous passageway 104.

In an alternative embodiment, conductive polymer electrodes 102 are press-fit into conduit 38, 50. In another alternative embodiment, conductive polymer electrodes 102 are solvent bonded and UV cured and cross-linked to conduit 38, 50.

In a further alternative embodiment, electrodes (not shown) are printed or deposited on the inner surface of conduit 38, 50, e.g., via a conductive ink in a screening or photolithographic process. For example, the ink can be applied in such a manner to a flexible membrane of disposable cassette 50 or other disposable plastic component of a medication delivery system.

Referring now to FIGS. 2 and 12, two disposable cassette-based electrical cells are illustrated by cells 100c and 100d. Cassette 50 generally models a Homechoice® APD system cassette marketed by the eventual assignee of the present disclosure. Cassette 50 in general includes a rigid structure having rigid outer walls 52a to 52d (referred to herein collectively as walls 52 or generally, individually as wall 52), rigid inner walls 54 (defining inner pump chambers P1 and P2 and inner fluid pathways such as pathway 104), rigid fluid ports 56 (connectable sealingly to tubing 38) and a pair of flexible membranes 58 sealed to outer rigid walls 52 and inner rigid walls 54. Suitable materials for the rigid portion of cassette 50 include medical grade engineered thermoplastics, e.g., polycarbonate, acrylic, cyclic olefins and their copolymers, thermoplastic elastomers, and their blends and alloys. Suitable materials for flexible membrane 58 include polyvinyl chloride, olefin, coextruded multi-layer films and micro-layer coextruded films (e.g., 10 to 1000 layers typically). It should be appreciated that the Homechoice® APD system cassette serves merely as an example and that other fluid pumping/valving cassette made of different materials can employ cells 100c and 100d.

Cell 100c is similar to cell 100a in that it employs cylindrical electrodes 102a and 102b that extend all the way across fluid pathway 104 and penetrate through slightly into inner wall 54a for the process control and accuracy reasons discussed above in connection with cell 100a. Upper, outer wall 52a can be molded sealingly around electrodes 102 or electrodes 102 can be sealed adhesively to upper, outer wall 52a of cassette 50. Press-fitting or other types of mechanical bonding can be used additionally or alternatively. Upper wall 52c can include or define ports or extensions 60a and 60b that provide additional surface area for cassette 50 to be sealed and crosslinked to the adhesive to seal to electrodes 102.

Electrodes 102 in cell 100c are again spared apart a distance L, have a contact length l, have a diameter $D_e$ and a contact surface area expressed as follows:

$$A_e = \pi * l * D_e$$

Hydraulic area $A_h$ of hydraulic pathway 104 in the illustrated embodiment is square or rectangular and can be expressed as follows:

$$A_h = l \times w$$

where w is the width of cassette 50 (see FIG. 2).

As seen in FIG. 2, when cassette 50 is loaded into cycler 12 of system 10, a door 62 is closed such that cassette 50 resides between door 62 and an inflexible bladder 64 of instrument 12. At this point, electrodes 102a and 102b may be loosely in contact with electrical leads or contacts 74a and 74b, respectively, mounted to the door 62 and shown in FIG. 3A in electrical communication with signal source 72. When inflatable bladder 64 is inflated, cassette 50 is pushed against door 62 causing electrodes 102a and 102b to make intimate contact with contacts 74a and 74b.

FIGS. 2 and 12, illustrate an alternative cassette-based electrical cell arrangement 100d. Cell 100d employs a layer of conductive ink stencil printed, screen printed or applied via a photolithographic process in a continuous manner onto inner and outer surfaces of flexible membrane 58 to form electrodes 102a and 102b. Suitable conductive inks are provided for example by carbon, conductive polymers, metalized inks, metal particle filled polymers, and nanoparticle filled conductive inks.

As before, electrodes 102a and 102b of cell 100d are separated by a hydraulic path length L. The contact area $A_e$ of electrodes 102 of cell 100d is the length l that the inked electrodes extend downwardly on the inner surface of membrane 58 multiplied by the width w of electrodes 102 on the inner surface of the membrane as seen in FIG. 12.

For cell 100d, when cassette 50 is loaded into cycler 12, door 62 is closed and inflatable bladder 64 is inflated, electrodes 102a and 102b, extending to the outer surface of membrane 58 are placed in intimate contact with leads or contacts 74a and 74b, respectively, mounted to pressure plate 66 shown in FIG. 2, and communicating electrically with signal source 72.

It is contemplated that the inked electrodes 102 of cell 100d are applied thinly enough that a standard flexible plastic membrane to rigid plastic piece bonding procedure, such as a heat seal, ultrasonic seal, solvent or adhesive bond is sufficient to seal the electrode areas of membrane 58 to upper, rigid plastic wall 52a. It may be necessary however to apply a local application of a sealant to the electrode areas to ensure a proper seal. The inked electrodes 102 of cell 100d are applied in a sufficient length l and width w to provide a sufficient amount conductive mass to carry the signal of source 72, which can be on the order of micro- or milli-Watts.

It should be appreciated that electrodes 102 of cell 100c and cell 100d can be placed in any suitable position, on any suitable wall 52 or membrane of cassette 50.

Figure 13:
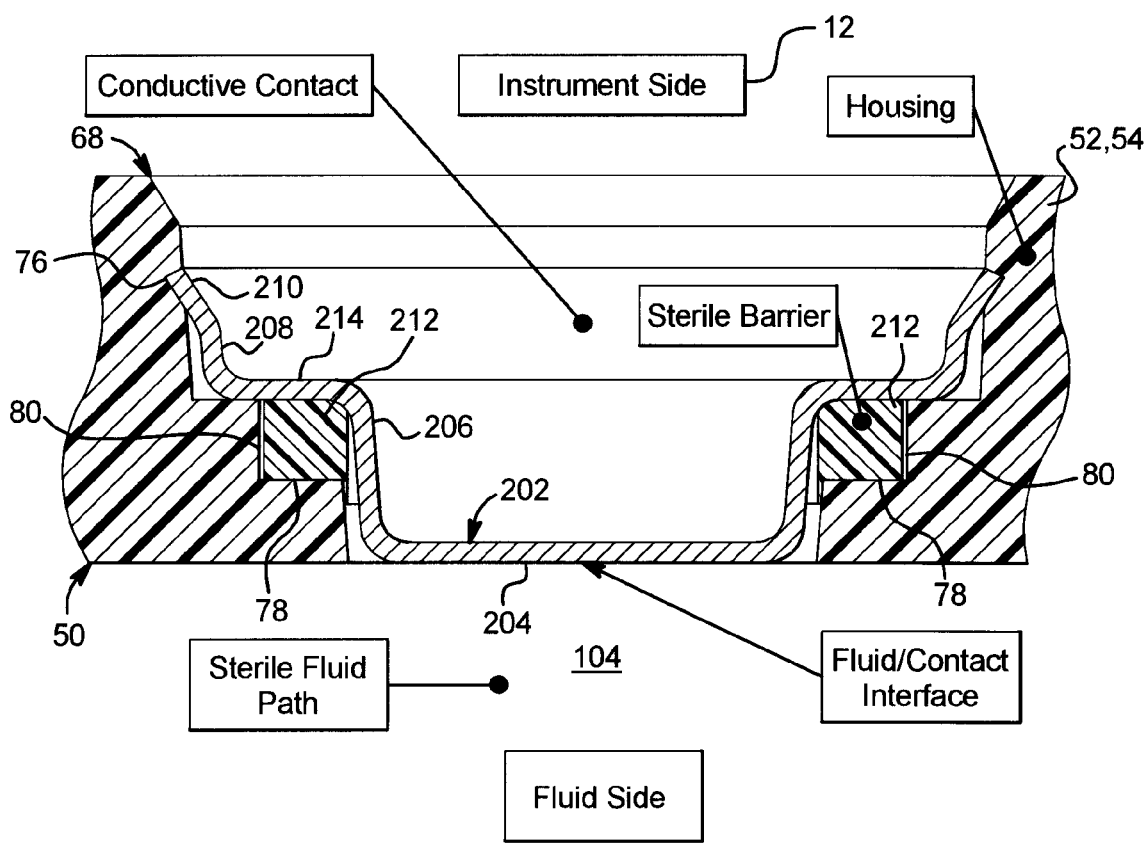
FIG. 13 is a side-sectioned view of one embodiment for a disposable conductive contact.

Referring now to FIG. 13, one preferred electrode 202 is illustrated. Electrode 202 of FIG. 13 is advantageous from a number of respects including, size, ease of manufacture and ease of installation with a fluid conduit, e.g., in communication with one of tubes 38 (FIG. 1) or fluid cassette 50. For ease of illustration, electrode 202 of FIG. 13 is shown as being inserted into one of the walls 52 or 54 of cassette 50.

Electrode 202 includes a fluid contact interface 204 extending to an annular sidewall 206, which extends upwardly to a retainer ring portion 208 of the electrode. Retainer 208 is bent and configured so as to be somewhat pliable and capable of being press-fit or frictionally engaged with a stepped or tapered aperture 68 formed in wall 52 and 54 of cassette 50. Stepped or tapered aperture 68 can provide or define an annular receiving groove 76, which is sized and shaped to snap-fittingly receive the upper edge 210 of retainer ring portion 208 of electrode 202. Thus when electrode 202 is pushed into stepped aperture 68, the sidewall of aperture 68 causes upper edge 210 of retainer ring 208 to bend inward until reaching receiving groove 76 of aperture 68. At this point, upper edge 210 snaps into groove 76, which holds electrode 202 sealingly in place. It should be appreciated however that in an alternative embodiment groove 76 is not provided, and wherein the seal instead relies on a press or interference fit between the wall of aperture 68 and upper edge 210 of electrode 202.

It may be that the apparatus and mechanical installation procedure of electrode 202 just described is enough to prevent (i) medical fluid or dialysate from escaping through the interface between retainer ring portion 208 and stepped aperture 66 of cassette 50 and (ii) air from outside cassette 50 from reaching sterile fluid in hydraulic pathway 104 without an additional sealing apparatus. Alternatively, a sterile sealing barrier 212, e.g., of an o-ring nature, is provided to prevent fluid or air from leaking out of or into, respectively, cassette 50. Still further alternatively, a suitably bondable adhesive or overmolding procedure discussed above can be employed.

Sealing ring 212 is made of a suitable medical grade compressible material, such as silicon, thermoplastic elastomer or isoprene. Flange portion 214 of electrode 202 compresses sealing ring 212 against stepped surface 78 of stepped or tapered aperture 68. It is also possible that sidewall 206 of electrode 202 can press sealing ring 212 outwardly against side surface 80 of stepped or tapered aperture 68.

Electrode 202 is made of stainless steel in one embodiment, e.g., for contacting fresh, sterile dialysate or other medicament. It is contemplated however to make electrode 202 and any of electrodes 102 described above from a different conductive material, such as a conductive polymer. Further, different metals could be used, such as copper or aluminum, for electrical or thermal sampling of a waste fluid, for example, such as fluid delivered from cassette 50, through drain line 38b to drain as shown in FIG. 1.

For conductivity sensing, contact 202 will have a contact area $A_e$, which is generally defined by the diameter $D_e$ of contact portion 204. Fluid flows through pathway 104 and contacts portion 204. Electrode 202 (e.g., pair of electrodes 202) is in turn connected electrically via a contact 74 (referring generally to one of contacts 74a and 74b), directly or indirectly, to signal source 72 located within instrument 12.

Alternatively, the pair of electrodes interfaces with a standalone hardware unit, such as cell holder 112 of FIG. 6.

As discussed above, it is contemplated to use any of electrodes 102 or electrodes 202 for multiple purposes, such as for a needle or catheter access disconnection system ("ADS"), temperature sensing, valve leak detection in addition to conductivity measurement. To this end, it is contemplated to use a single one or a single pair of electrodes 102 or 202 for multiple purposes or to dedicate an electrode 102 or 202 or electrode pair to a single use.

In a multi-use example, a pair of electrodes 102 or 202 can be used to detect conductivity at the beginning of each bagged dialysis cycle (e.g. peritoneal dialysis or bagged hemodialysis solution) to ensure that the dialysate through a hydraulic pathway 104 (e.g., from dual chamber bags 32) has been mixed properly. After this determination has been made, contacts 202 can then be used to sense an impedance of the dialysate through hydraulic pathway 104 as disclosed in the '110 application referenced above for ADS purposes. Conductivity sensing and ADS sensing in one embodiment both require that at least one signal be injected through electrodes 202 to the dialysate. The same signal source 72 may be used, however, a different and/or additional signal source could be provided. The different sensing requires different signal processing, e.g., software.

At the same time or in a different application, a separate dedicated pair of electrodes 202 can be provided, e.g., at the to- and from-heater bag ports 56 for temperature sensing and heater control. Alternatively, the temperature sensing and heating sensing system could use a single electrode 202 at, e.g., from-heater port 56. The Homechoice® APD system and associated disposable cassette illustrated throughout this application uses a batch heating system via a warmer bag 36 shown in FIG. 1. Electrodes 102 and 202 can be used alternatively with an in-line heating system, for example by placing electrodes 102 and 202 upstream and downstream of an in-line fluid heating pathway.

Figure 15:
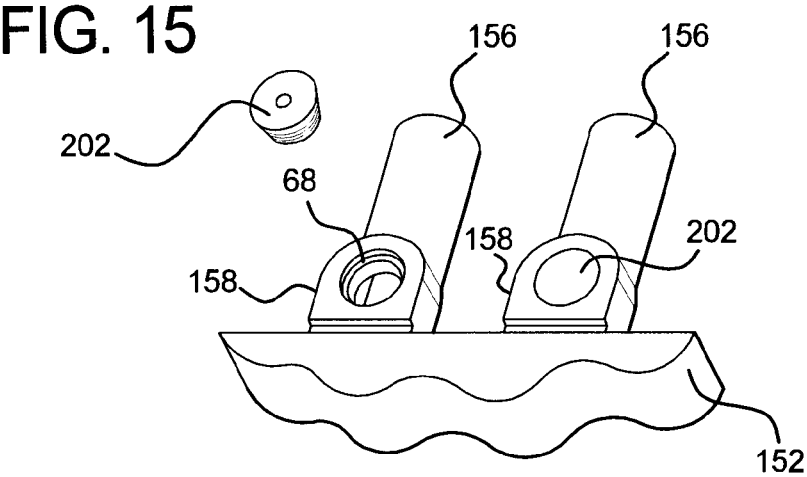
FIGS. 14 and 15 are perspective views showing an embodiment for placing the disposable conductive contact of FIG. 13 in position for a needle/catheter access disconnection or valve leak detection.
Figure 14:
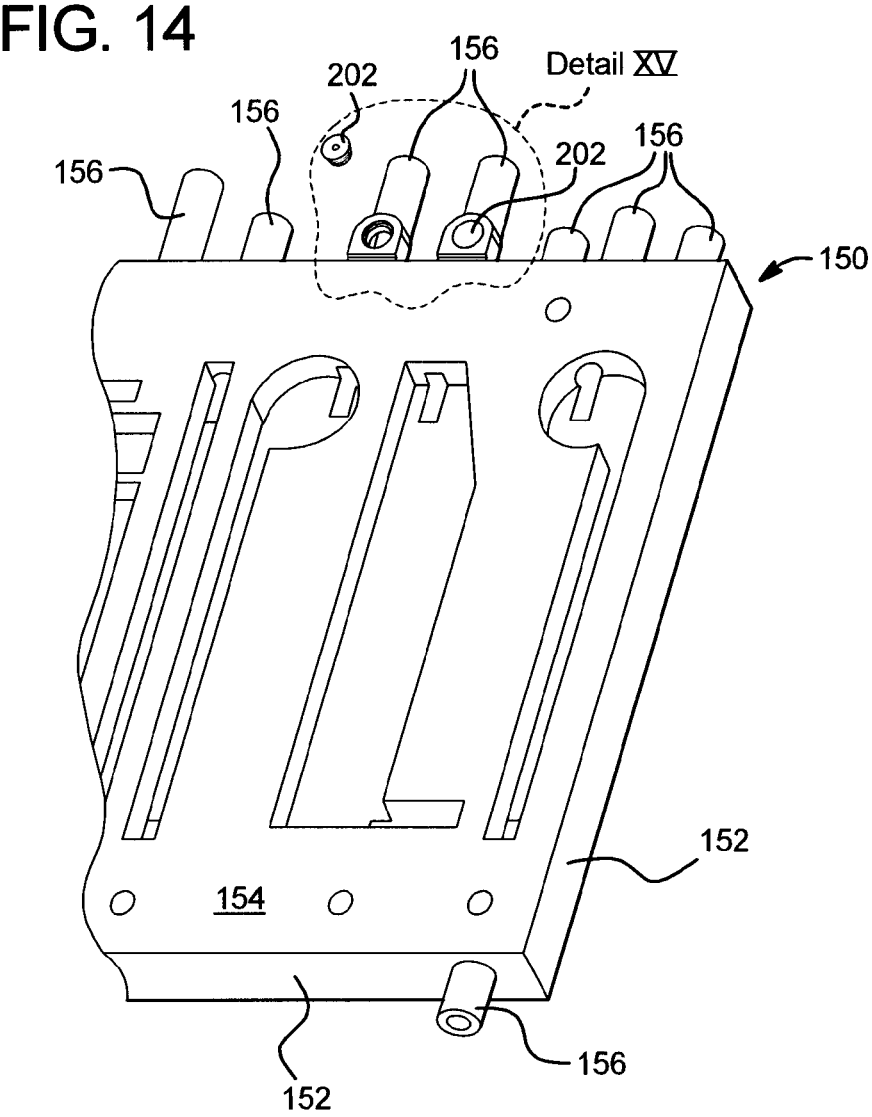

Referring now to FIGS. 14 and 15, an alternative configuration for installing electrodes 202 into a disposable cassette is illustrated. Here, alternative cassette 150 includes rigid sidewalls 152 having or providing a plurality of fluid ports 156 and a top wall 154 defining or including various apertures and fluid pathways. Two of ports 156 shown in FIG. 14 are shown in Detail XV in FIG. 15 as including bulkheads 158. Bulkheads 158 include or define stepped or tapered electrode receiving apertures 68, described above, which receive electrodes 202.

Ports 156 having bulkhead 158 receiving electrodes 202 can be, for example, to- and from-patient ports 156, at which system 10 tests for an access disconnection. Alternatively, the bulkhead ports 156 are any that are any downstream of one or more valve seat of cassette 150, wherein system 10 uses those electrodes 202 to determine if any valve seat or corresponding valve actuator is not functioning properly. Or, bulkhead ports 156 can be supply ports upstream of the cassette valves for conductivity sensing, wherein the valves can virtually immediately be closed to stop flow of improperly mixed fluid through cassette 156 (or improper dose or type of drug in a drug infusion machine) when such a situation is sensed.

Figure 16:
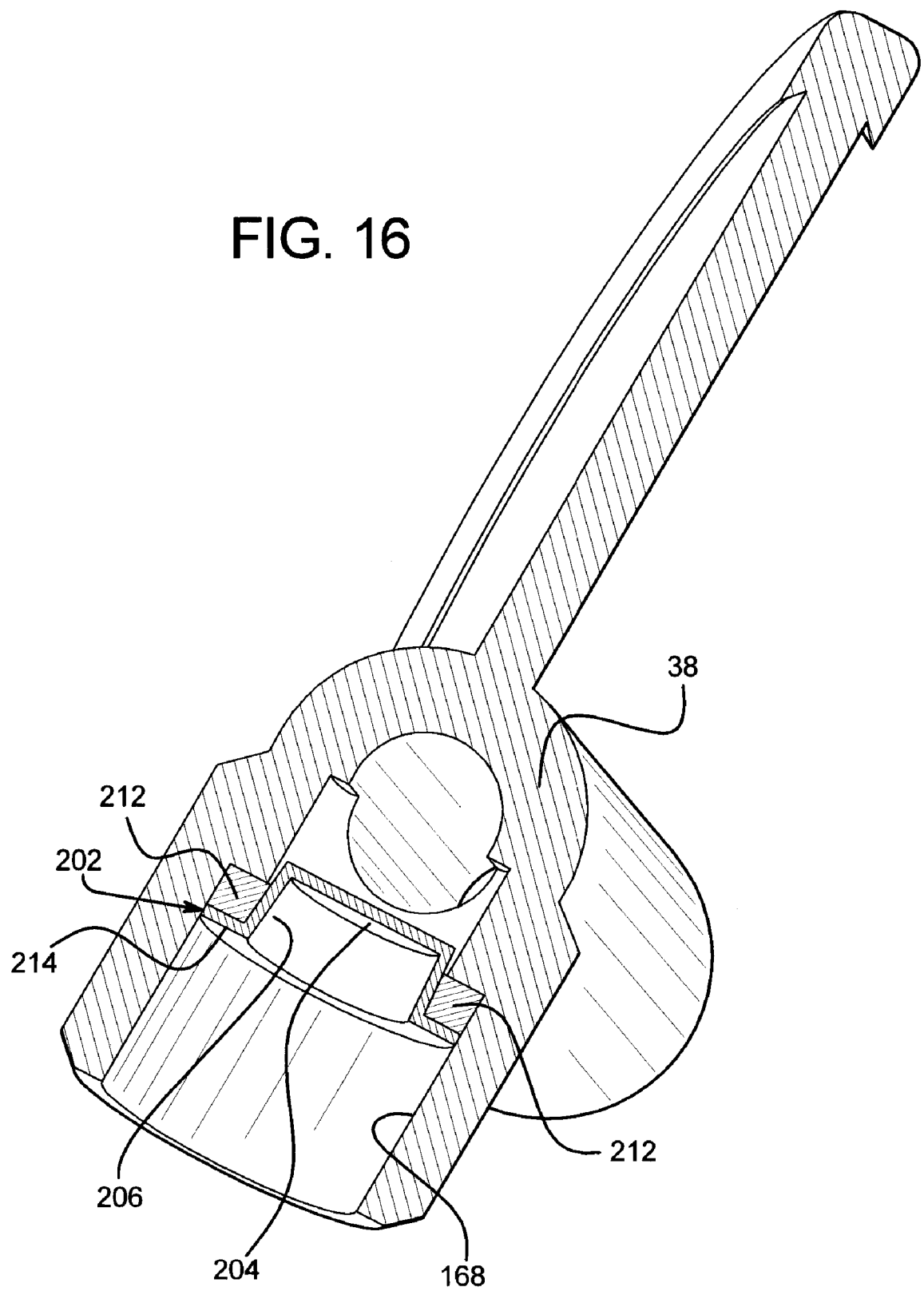
FIG. 16 is a cutaway perspective view showing an embodiment for placing the disposable conductive contact of FIG. 13 in communication with fluid flowing through a tube or conduit.

Referring now to FIG. 16, an embodiment for installing electrode 202 into a tube or conduit 38 is illustrated. Here, tube or conduit defines or includes an alternative aperture 168, which has an at least substantially uniform inner diameter. In an alternative embodiment, tube or conduit 38 includes or defines tapered aperture 68. Electrode 202 is press-fit, overmolded into and/or solvent bonded to aperture 168 as has been described herein.

Electrode 202 in conduit 38 can be used alone or in a pair of electrodes 202 for any one or more of the functions described herein. Electrode 202 is made of any of the materials discussed herein.

Electrode 202 is different than that of FIG. 13. As before, electrode 202 includes a fluid contact interface 204, an annular sidewall 206 and a flange portion 214. Here, however, retention ring portion 208 discussed above is not provided. Instead, flange portion 214 is sized to be slightly wider than the inner diameter of aperture 168. Aperture 168 can define a groove, similar to groove 76 of FIG. 13, into which the outer edge of flange portion 214 snap-fits for permanent or semi-permanent installation into tube or conduit 35.

Tube or conduit 38 can be formed integrally with an elongated section of tubing or conduit. Alternatively, tube or conduit 38 in FIG. 16 is configured to seal, semi-permanently or permanently with one or more section of elongated tubing or conduit.

Figure 17:
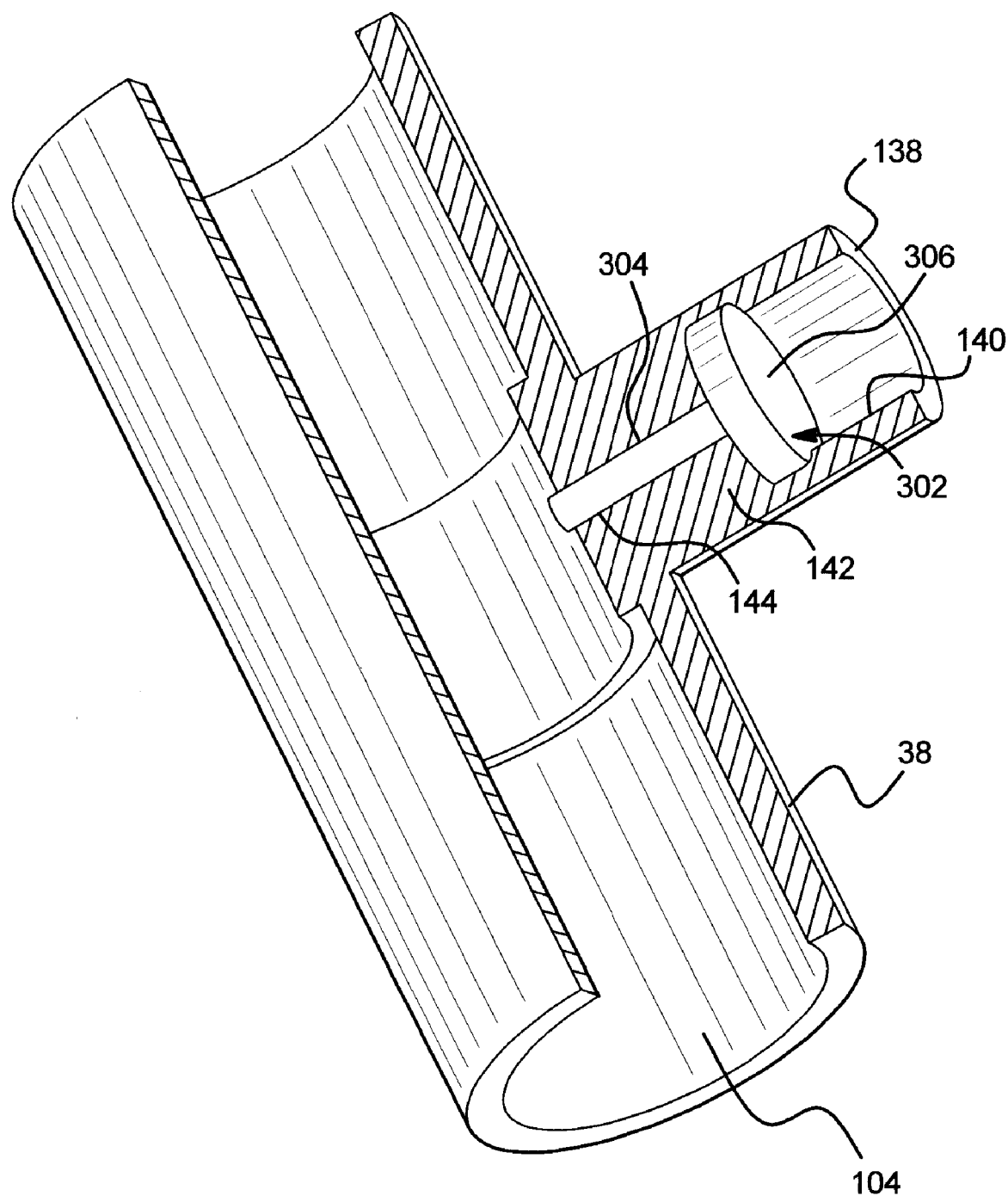
FIG. 17 is a perspective view of another embodiment for a disposable conductive contact.

Referring now to FIG. 17, electrode 302 illustrates a further alternative electrode configuration. Here tube 38 is formed with or connected to a T-extension 138. T-extension 138 defines an aperture 140 into which electrode 302 is placed. Electrode 302 includes a stem 304 and a head 306. Head 306 bottoms out against a seat 142 of T-extension 138. Seat 142 defines a cylindrical aperture 144 through which stem 304 of electrode 302 is inserted. In an embodiment, a diameter of aperture 144 is smaller than that of stem 304, such that a compression seal is formed. Further sealing can be provided via overmolding and/or bonding as has been described herein.

The length of stem 304 and aperture 144 are controlled such that stem 304 extends into pathway 104 a precise, controlled and repeatable distance. Electrode 302 is used alternatively with a disposable cassette, such as cassette 50 or 150. Electrode 302 can be any of the materials described herein and operate alone or in a pair (e.g., as a cell).

In any of the embodiments described herein, instrument 12 or separate hardware unit can interfere with electrodes 102, 202, 302 through physical contact, such as via a conductive pin, or can be non-physically coupled, e.g., through an infrared or other type of energy sensor. For temperature sensing, an infrared ("IR") temperature sensor can be pointed towards head 306 of electrode 302 to non-mechanically or non-physically sense a temperature of head 306 and fluid flowing past stem 304 of electrode 302 indirectly.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   a dialysis instrument;
   a disposable pumping cassette apparatus operable with a pumping actuator of the dialysis instrument, the disposable cassette including an electronic cell, the electronic cell including a first and second electrode; and
   electronics associated with the electronic cell, the electronics including a source configured to provide one of a current and a voltage signal to at least one of the first and second electrodes, a measuring device configured to determine a resistance of a solution between the first and second electrodes by measuring the other of the current and the voltage signal, and a meter connected to the first and second electrodes and configured to protect the system against or to alert the system of a faulty connection between at least one of the first and second electrodes and the source.

2. The dialysis system of claim 1, wherein the dialysis system is of a type selected from the group consisting of: peritoneal dialysis, hemodialysis and colorectal dialysis.

3. The dialysis system of claim 1, wherein the electronics are further configured to use the electronic cell to determine if the solution has been mixed properly.

4. The dialysis system of claim 3, the electronics operable with the dialysis instrument upon determining that the solution has not been mixed properly to cause at least one of: (i) an alarm to be sounded; (ii) a visual message to be posted; (iii) a pump to be stopped; (iv) a line to be occluded; and (v) a valve to be closed.

5. The dialysis system of claim 1, wherein the electronics are further configured to use the electronic cell to identify the solution as one from the group consisting of: a dialysis fluid, a parenteral compounding fluid, an intravenous infusion fluid and a chemotherapeutic compounding fluid.

6. The dialysis system of claim 1, wherein the electronics are further configured to use the electronic cell to determine at least one of: (i) whether a connection between the dialysis instrument and a patient has been disconnected; (ii) a temperature of the solution; and (iii) a leaking valve.

7. The dialysis system of claim 1, wherein the first and second electrodes are at least one of: (i) formed of stainless steel; (ii) insert molded within the disposable apparatus; (iii) attached to the disposable apparatus by way of adhesive bonding; (iv) formed of electrically conductive plastic; (v) printed in a spaced apart relationship on a surface of the disposable apparatus; (vi) attached to the cassette of the disposable apparatus; (vii) attached to a section of tubing of the disposable apparatus; (viii) tapered to mate with tapered apertures of the disposable apparatus; (ix) invasive relative to the solution; and (x) protected against faulty connection with the instrument.

8. The dialysis system of claim 1, wherein at least one of: (i) the signal has a frequency of about 10,000 Hz or less; (ii) the measured resistance is proportional to a conductivity of said medical fluid; (iii) the electronics are configured to calculate a conductivity of the solution by applying an algorithm to the measured resistance; (iv) the conductivity is linearly proportional to a concentration of a substance within the solution.

9. The dialysis system of claim 8, the algorithm accounting for a temperature of the solution.

10. The dialysis system of claim 1, the electronics configured to perform a matching check using the electrical property of the solution.

11. The dialysis system of claim 10, wherein the matching check is at least one of: (i) used to determine whether the solution includes a particular substance; (ii) used to compare a conductivity of the solution with an acceptable range of conductivities; and (iii) performed by comparing the concentration to at least one value in a look-up table stored in a database.

12. The dialysis system of claim 1, the electronics configured to sense whether an expected step change in conductivity occurs after a period of time to determine if the solution can be delivered to a patient.

13. A dialysis system comprising:
a dialysis instrument;
a disposable cassette operable with the dialysis instrument, the disposable cassette including a rigid structure, the rigid structure including first and second apertures each defined by a non-uniform wall, each non-uniform wall defining a receiving structure;
first and second conductive contacts having non-uniform shapes that mate with the non-uniform walls of the first and second apertures, each non-uniform shape including a retainer ring portion, wherein each receiving structure is sized and shaped to snap-fittingly receive one of the retainer ring portions; and
electronics operable with the first and second contacts to determine at least one of: (i) a patient access disconnection; (ii) a temperature of a medical fluid flowing through the cassette; and (iii) a conductivity of the medical fluid flowing through the cassette.

14. The dialysis system of claim 13, wherein the electronics are operable with the first and second contacts to detect at least two of: (i) a patient access disconnection; (ii) a temperature of a medical fluid flowing through the cassette; and (iii) a conductivity of the medical fluid flowing through the cassette.

15. The dialysis system of claim 13, wherein the electronics are operable with the first and second contacts to detect each of: (i) a patient access disconnection; (ii) a temperature of a medical fluid flowing through the cassette; and (iii) a conductivity of the medical fluid flowing through the cassette.

16. The dialysis system of claim 13, wherein the non-uniform shapes of the contacts and the non-uniform walls are at least one of: (i) tapered and (ii) stepped.

17. The dialysis system of claim 13, which includes a sterile barrier placed between the contacts and the defining walls of the disposable cassette.

18. The dialysis system of claim 13, wherein the rigid structure of the disposable cassette is one of: (i) part of a valve and flowpath portion of the cassette; and (ii) includes first and second ports extending from the cassette.

19. The dialysis system of claim 13, wherein the dialysis system is of a type selected from the group consisting of: peritoneal dialysis, hemodialysis and colorectal dialysis.

20. The dialysis system of claim 13, wherein the electronics include a source configured to provide one of a current and a voltage signal to at least one of the first and second electrodes, and a measuring device configured to measure a resistance of the solution between the first and second electrodes.

21. The dialysis system of claim 20, wherein at least one of: (i) the signal has a frequency of about 10,000 Hz or less; (ii) the measured resistance is proportional to a conductivity of said medical fluid; (iii) the electronics are configured to calculate a conductivity of the solution by applying an algorithm to the measured resistance; (iv) the conductivity is linearly proportional to a concentration of a substance within the solution; and (v) a second meter is connected to the first and second electrodes and is configured to protect the system against or to alert the system of a faulty connection between at least one of the first and second electrodes and the instrument.

* * * * *